(12) United States Patent
Estell et al.

(10) Patent No.: US 6,835,550 B1
(45) Date of Patent: Dec. 28, 2004

(54) MUTANT PROTEINS HAVING LOWER ALLERGENIC RESPONSE IN HUMANS AND METHODS FOR CONSTRUCTING, IDENTIFYING AND PRODUCING SUCH PROTEINS

(75) Inventors: David A. Estell, San Mateo, CA (US); Fiona A. Harding, Santa Clara, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/060,872

(22) Filed: Apr. 15, 1998

(51) Int. Cl.[7] .......................... C12N 5/00; G01N 33/53
(52) U.S. Cl. ...................... 435/7.24; 435/377; 435/395
(58) Field of Search ............................. 435/7.24, 327, 435/395

(56) References Cited

U.S. PATENT DOCUMENTS

| | | | | |
|---|---|---|---|---|
| 5,585,250 A | * | 12/1996 | Garrity et al. | 435/69.3 |
| 5,593,877 A | * | 1/1997 | King | 435/197 |
| 5,648,219 A | * | 7/1997 | Mackay et al. | 435/6 |
| 5,820,862 A | * | 10/1998 | Garman et al. | 424/184.1 |
| 5,849,589 A | * | 12/1998 | Tedder et al. | 435/377 |
| 5,994,126 A | * | 11/1999 | Steinman et al. | 435/325 |

FOREIGN PATENT DOCUMENTS

| | | |
|---|---|---|
| EP | 0 006 638 | 1/1980 |
| EP | 0 699 755 | 3/1996 |
| WO | WO 92/10755 | 6/1992 |
| WO | WO 96/16177 | 5/1996 |
| WO | WO 96/34946 | 11/1996 |
| WO | WO 97/30148 | 8/1997 |
| WO | WO 98/20116 | 5/1998 |
| WO | WO 98/52976 | 11/1998 |
| WO | WO 99/53038 | 10/1999 |
| WO | WO 99/61637 | 12/1999 |

OTHER PUBLICATIONS

Bhardwaj et al, Jour. Clin. Invest., 94, 797–807, 1994.*
Herbert et al, Dictionary of Immunology, 3rd Ed., Blackwell Scientific Publications, p. 153, 1985.*
Thomas, CL, *Taber's Cyclopedic Medical Dictionary*, F.A. Davis Company, p. A–79, 1981.*
Fehlner, PF, *Journal of Immunology*, 146, 799–806, 1991.*
Copy of PCT partial search for PCT/US 01/30062.
Graziano et al., "Enhancing the Immunogenicity of a Permissive Binding T Cell Epitope derived from the Simian Immunodeficiency Virus–Encoded Negative Regulatory Factor," *J. of Immun.*, V. 149, No. 2, 1991, pp. 556–561.
Lipford et al., "Peptide engineering allows cytotoxic T–cell vaccination against human papilloma virus tumour antigen, E6", Abstract, Database accession No. PREV199598171988.
Czerniecki, et al., *J. of Immunol.* 159:3823 (1997).
Macatonia, et al., *Immunol.* 74:399 (1991).
Mehta–Damani, et al., *Eur. J. Immunol.* 25:1206 (1995).
Schlienger, et al., *Blood* 96:3490 (2000).
Takamizawa, et al., *J. of Immunol.* 158:2134 (1997).
Zhou & Tedder, *Proc. Nat'l Acad. Sci. USA* 93:2588 (1996).
Gundlach et al., "Determination of T cell epitopes with random peptide libraries," *Journal of Immunological Methods*, V. 192 (1996) pp. 149–155.
Copy of PCT search report.

* cited by examiner

*Primary Examiner*—David Saunders
(74) *Attorney, Agent, or Firm*—Genencor International, Inc.

(57) ABSTRACT

The present invention relates to a novel improved protein mutant which produces low allergenic response in humans compared to the parent of that mutant. Specifically, the present invention comprises neutralizing or reducing the ability of T-cells to recognize epitopes and thus prevent sensitization of an individual to the protein.

14 Claims, 15 Drawing Sheets

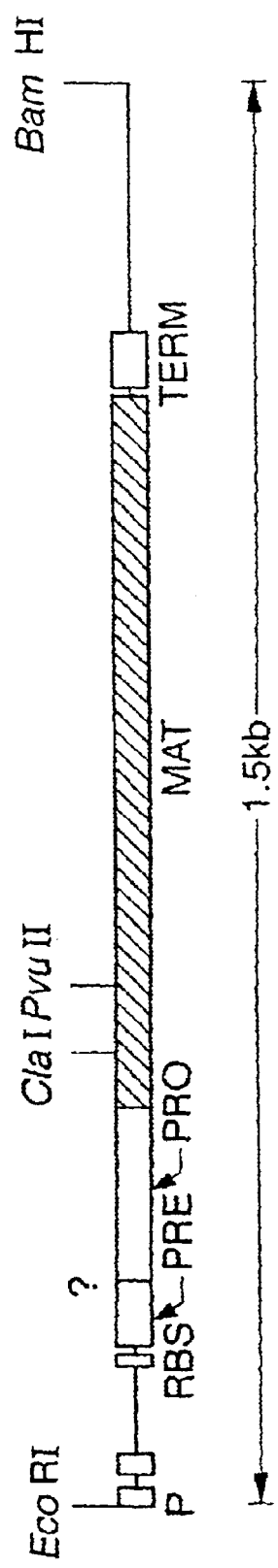
FIG._1A

```
                                                                                              -107
                                                                                              Met
                                         RBS
    GGTCTACTAAAATATTCCATACTATACAATTAATACACAGAATAATCTGTCTATTGGTTATTCTGCAATGAAAAAAGGAGAGGATAAGA GTG
1

P                                      PRE
    Arg Gly Lys Lys Val Trp Ile Ser Leu Leu Phe Ala Leu Phe Thr Met Ala Phe Gly Ser Thr Ser
99  AGA GGC AAA AAA GTA TGG ATC AGT CTG TTG GCT TTT ACG ATG GCG TTC GGC AGC ACA TCC

-80                             -70                         -60
    Ser Ala Gln Ala Ala Gly Lys Lys Lys Glu Gly Phe Lys Gln Thr Met Ser Thr Met
174 TCT GCC CAG GCG GCA GGG AAA AAG AAA GAA GGG TTT AAA CAG ACA AGC ATG ACG

-50                         PRO       -40
    Ser Ala Lys Ala Thr Leu Asn Ile Ser Val Asp Val Ile Tyr Lys Val Gln Phe Lys Tyr Val Asp Ala
249 AGC GCC GCT ACA TTA AAC ATT TCT GTA GAT GTC ATT TAT AAG GTC CAA TTC AAA TAT GTA GAC GCA

MAT                       -20                     -10
    Ala Ser Ala Thr Leu Asn Gln Lys Val Ala Val Lys Glu Leu Lys Lys Asp Pro Ser Val Ala Leu His Ser Gln
324 GCT TCA GCT ACA TTA AAC CAG AAA GTA GCT GTA AAA GAA TTG AAA AAA GAC CCG AGC GTC GCT CTG CAC TCT CAA

-1  1                              10                          40
    His Val Ala Tyr Ala Gln Ser Val Pro Tyr Gly Val Ser Gln Ile Lys Ala Pro Ala Leu His Ser Gln
399 CAC GTA GCA TAT GCG CAG TCC GTG CCT TAC GGC GTA TCA CAA ATT AAA GCC CCT GCT CTG CAC TCT CAA 20                                30                              40
    Gly Tyr Thr Gly Ser Asn Val Lys Val Ala Val Ile Asp Ser Gly Ile Asp Ser Ser His Pro Asp Leu Lys Val
474 GGC TAC ACT GGA AAT GTA AAG GTT GCG GTT ATC GAC AGC GGT ATC GAT TCT TCT CAT CCT GAT TTA AAG GTA
```

| | | | | | | | | | | | | | | Asp 60 Asn AAC | Asn AAC | Ser TCT | His CAC | Gly GGA | Thr ACT | His CAC | Val GTT | Ala GCC |
|---|---|---|---|---|---|---|---|---|---|---|---|---|---|---|---|---|---|---|---|---|---|---|

549 Ala GCA Gly GGC Gly GGA Ala GCC Ser AGC Met ATG Val GTT Pro CCT Ser TCT Glu GAA Thr ACA Pro CCT Asn AAT Phe TTC Gln CAA Asp GAC Asn AAC Asn AAC Ser TCT His CAC Gly GGA Thr ACT His CAC Val GTT Ala GCC

624 Gly GGT 70 Thr ACA Val GTT Ala GCG Leu CTT Asn AAT Asn AAC Ser TCA Glu GAA 80 Ile ATC Gly GGT Val GTA Leu TTA Gly GGC Val GTT Ala GCG Pro CCA Ser AGC Ser AGC Ala GCA 90 Ser TCA Leu CTT Tyr TAC Ala GCT Val GTA Lys AAA

699 Val GTT Leu CTC Gly GGT Asp GAT Asp GCT Ala GCT Ala Gly GGT Ser TCC Gln CAA Tyr TAC Trp TGG Ile ATC 110 Asn AAC Ile ATT Ala GCA Glu GAG Trp TGG 100 Ala GCG Ala GCA Ala GCA Ile ATC Ala GCA Asn AAC Asn AAC Met ATG

774 Asp GAC Val GTT Ile ATT Asn AAC Met ATG 120 Ser AGC Leu CTC Gly GGC Gly GGA Pro CCT Ser TCT Gly GGT Ser TCC 130 Ala GCT Leu TTA Lys AAA Ala GCG 140 Asp GAT Val GTT Lys AAA Ala GCC Val GTT Ala GCA

849 Ser TCC Gly GGC Val GTA Val GTC Val GTA Ile ATT 150 Ala GCA Ala GCA Val GTT Ala GCA Ala GCG Ser TCC Thr ACT Thr ACA Ser TCC 160 Gly GGC Ser AGC Ser TCA Ala GCA Ala GCA Phe TTC 190 Ser TCA Tyr TAC Pro CCT Gly GGT

924 Lys AAA 170 Tyr TAC Pro CCT Ser TCT Ile ATT Met ATG Ala GCA Val GTA Gly GGC Ala GCA Val GTT Gly GGC Asp GAC Asn AAC Glu GAA Ser AGC 180 Ser AGC Asn AAC Arg AGA Gln CAA Ala GCA Ala GCA Ser TCT Lys AAA Val GTA Gly GGA Pro CCT

999 Glu GAG Leu CTT Asp GAT Val GTC Met ATG Ala GCA 200 Pro CCT Gly GGC Val GTA Ser TCT Ile ATC Gln CAA Ser TCT Leu ACG 210 Pro CCT Gly GGA Asn AAC Lys AAA Ala GCG Tyr TAC Gly GGG Ala GCA Tyr TAC Asn AAC Gly GGT

1074 Thr ACG 220 Ser TCA Met ATG Ala GCA Ser TCT Pro CCG His CAC Val GTT Ala GCC Gly GGA 230 Ala GCG Ala GCT Leu TTG Ile ATT Leu CTT Ser TCT Lys AAG His CAC Pro CCG Asn AAC Trp TGG 240 Thr ACA Asn AAC Thr ACT

```
                                         250  Gln                              260
     Gln Val Arg Ser Ser Ser Leu Glu Asn Thr Thr Thr Lys Leu Gly Asp Ser Phe Tyr
1149 CAA GTC CGC AGC AGT TTA GAA AAC ACC ACT ACA AAA CTT GGT GAT TCT TTC TAC

Tyr Gly Lys Gly Leu Ile Asn
     TAT GGA AAA GGG CTG ATC AAC 270           275                   TERM
     Val Gln Ala Ala Ala Gln OC
1224 GTA CAG GCA GCT GCA CAG TAA AACATAAAAAAACCGGGCCTTGGCCCCCGGTTTTTATTTTCTTCCTCCGATGTTCAATCCGCTCC

1316 ATAATCGACGGATGGCTCCCCTGAAAATTTTAACGAGAAACGGGGTTGACCCGGCTCAGTCCCGTAACGGCCAAGTCCTGAAACGTCTCAATCGCCG

1416 CTTCCCGGGTTTCCGGTCAGCTCAATGCCGTAACGGTCGGGGCGGTTTTCCTGATACCGGGAGACGGCATTCGTAATCGGATC
```

CONSERVED RESIDUES IN SUBTILISINS FROM
*BACILLUS AMYLOLIQUEFACIENS*

COMPARISION OF SUBTILISIN SEQUENCES FROM:
B.amyloliquefaciens
B.subtilis
B.licheniformis
B.lentus

| FIG._3A |
| FIG._3B |

*FIG._3*

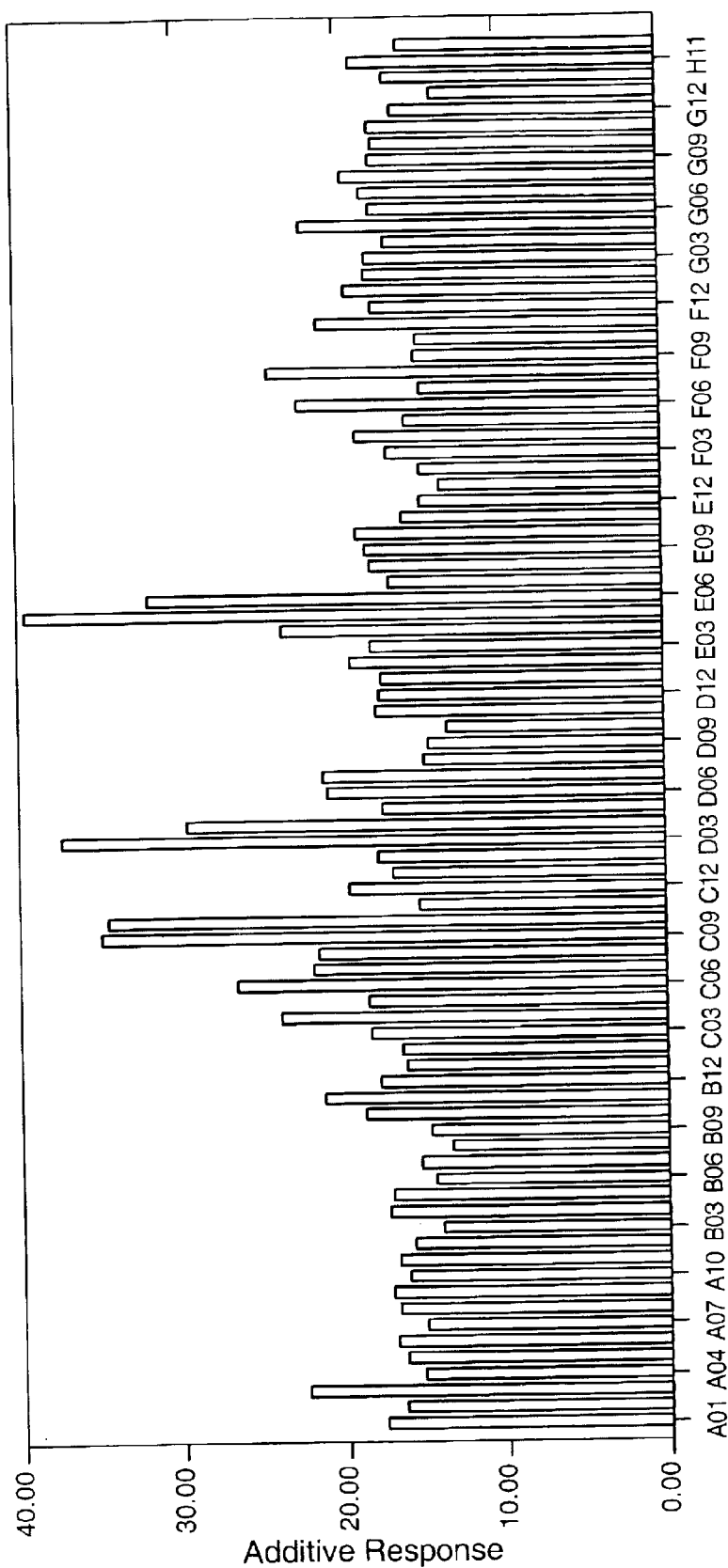
FIG._4

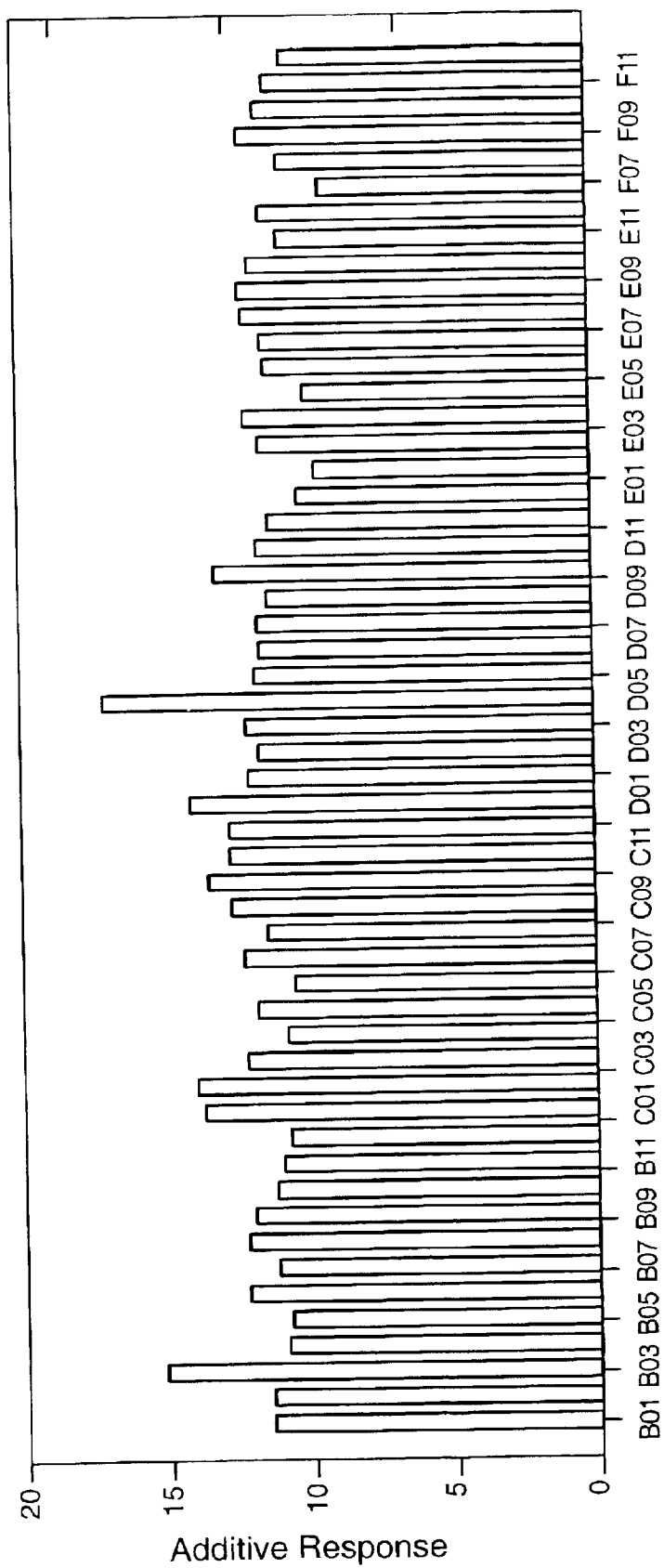
FIG._5

| # | ID | Sequence | # | ID | Sequence |
|---|---|---|---|---|---|
| 1 | A12 | IKDFHVYFRESRDAG | 49 | E12 | SATSRGVLVVAASGN |
| 2 | A11 | LEQAVNSATSRGVLV | 50 | E11 | SRGVLVVAASGNSGA |
| 3 | A10 | AQSVPWGISRVQAPA | 51 | E10 | VLVVAASGNSGAGSI |
| 4 | A9 | VPWGISRVQAPAAHN | 52 | E9 | VAASGNSGAGSISYP |
| 5 | A8 | GISRVQAPAAHNRGL | 53 | E8 | SGNSGAGSISYPARY |
| 6 | A7 | RVQAPAAHNRGLTGS | 54 | E7 | SGAGSISYPARYANA |
| 7 | A6 | APAAHNRGLTGSGVK | 55 | E6 | GSISYPARYANAMAV |
| 8 | A5 | AHNRGLTGSGVKVAV | 56 | E5 | SYPARYANAMAVGAT |
| 9 | A4 | RGLTGSGVKVAVLDT | 57 | E4 | ARYANAMAVGATDQN |
| 10 | A3 | TGSGVKVAVLDTGIS | 58 | E3 | ANAMAVGATDQNNNR |
| 11 | A2 | GVKVAVLDTGISTHP | 59 | E2 | MAVGATDQNNNRASF |
| 12 | A1 | VAVLDTGISTHPDLN | 60 | E1 | GATDQNNNRASFSQY |
| 13 | B12 | LDTGISTHPDLNIRG | 61 | F12 | DQNNNRASFSQYGAG |
| 14 | B11 | GISTHPDLNIRGGAS | 62 | F11 | NNRASFSQYGAGLDI |
| 15 | B10 | THPDLNIRGGASFVP | 63 | F10 | ASFSQYGAGLDIVAP |
| 16 | B9 | DLNIRGGASFVPGEP | 64 | F9 | SQYGAGLDIVAPGVN |
| 17 | B8 | IRGGASFVPGEPSTQ | 65 | F8 | GAGLDIVAPGVNVQS |
| 18 | B7 | GASFVPGEPSTQDGN | 66 | F7 | LDIVAPGVNVQSTYP |
| 19 | B6 | FVPGEPSTQDGNGHG | 67 | F6 | VAPGVNVQSTYPGST |
| 20 | B5 | GEPSTQDGNGHGTHV | 68 | F5 | GVNVQSTYPGSTYAS |
| 21 | B4 | STQDGNGHGTHVAGT | 69 | F4 | VQSTYPGSTYASLNG |
| 22 | B3 | DGNGHGTHVAGTIAA | 70 | F3 | TYPGSTYASLNGTSM |
| 23 | B2 | GHGTHVAGTIAALNN | 71 | F2 | GSTYASLNGTSMATP |
| 24 | B1 | THVAGTIAALNNSIG | 72 | F1 | YASLNGTSMATPHVA |
| 25 | C12 | AGTIAALNNSIGVLG | 73 | G12 | LNGTSMATPHVAGAA |
| 26 | C11 | IAALNNSIGVLGVAP | 74 | G11 | TSMATPHVAGAAALV |
| 27 | C10 | LNNSIGVLGVAPSAE | 75 | G10 | ATPHVAGAAALVKQK |
| 28 | C9 | SIGVLGVAPSAELYA | 76 | G9 | HVAGAAALVKQKNPS |
| 29 | C8 | VLGVAPSAELYAVKV | 77 | G8 | GAAALVKQKNPSWSN |
| 30 | C7 | VAPSAELYAVKVLGA | 78 | G7 | ALVKQKNPSWSNVQI |
| 31 | C6 | SAELYAVKVLGASGS | 79 | G6 | KQKNPSWSNVQIRNH |
| 32 | C5 | LYAVKVLGASGSGSV | 80 | G5 | NPSWSNVQIRNHLKN |
| 33 | C4 | VKVLGASGSGSVSSI | 81 | G4 | WSNVQIRNHLKNTAT |
| 34 | C3 | LGASGSGSVSSIAQG | 82 | G3 | VQIRNHLKNTATSLG |
| 35 | C2 | SGSGSVSSIAQGLEW | 83 | G2 | RNHLKNTATSLGSTN |
| 36 | C1 | GSVSSIAQGLEWAGN | 84 | G1 | LKNTATSLGSTNLYG |
| 37 | D12 | SSIAQGLEWAGNNGM | 85 | H12 | TATSLGSTNLYGSGL |
| 38 | D11 | AQGLEWAGNNGMHVA | 86 | H11 | SLGSTNLYGSGLVNA |
| 39 | D10 | LEWAGNNGMHVANLS | 87 | H10 | STNLYGSGLVNAEAA |
| 40 | D9 | AGNNGMHVANLSLGS | 88 | H9 | NLYGSGLVNAEAATR |
| 41 | D8 | NGMHVANLSLGSPSP | | | |
| 42 | D7 | HVANLSLGSPSPSAT | | | |
| 43 | D6 | NLSLGSPSPSATLEQ | | | |
| 44 | D5 | LGSPSPSATLEQAVN | | | |
| 45 | D4 | PSPSATLEQAVNSAT | | | |
| 46 | D3 | SATLEQAVNSATSRG | | | |
| 47 | D2 | LEQAVNSATSRGVLV | | | |
| 48 | D1 | AVNSATSRGVLVVAA | | | |

FIG._6A

| | | | | | |
|---|---|---|---|---|---|
| 1 | A12 | IKDFHVYFRESRDAG | 49 | E12 | KKIDVLNLSIGGPDF |
| 2 | A11 | DAELHIFRVFTNNQV | 50 | E11 | DVLNLSIGGPDFMDH |
| 3 | A10 | PLRRASLSLGSGFWH | 51 | E10 | NLSIGGPDFMDHPFV |
| 4 | A9 | RASLSLGSGFWHATG | 52 | E9 | IGGPDFMDHPFVDKV |
| 5 | A8 | LSLGSGFWHATGRHS | 53 | E8 | PDFMDHPFVDKVWEL |
| 6 | A7 | GSGFWHATGRHSSRR | 54 | E7 | MDHPFVDKVWELTAN |
| 7 | A6 | FWHATGRHSSRRLLR | 55 | E6 | PFVDKVWELTANNVI |
| 8 | A5 | ATGRHSSRRLLRAIP | 56 | E5 | DKVWELTANNVIMVS |
| 9 | A4 | RHSSRRLLRAIPRQV | 57 | E4 | WELTANNVIMVSAIG |
| 10 | A3 | SRRLLRAIPRQVAQT | 58 | E3 | TANNVIMVSAIGNDG |
| 11 | A2 | LLRAIPRQVAQTLQA | 59 | E2 | NVIMVSAIGNDGPLY |
| 12 | A1 | AIPRQVAQTLQADVL | 60 | E1 | MVSAIGNDGPLYGTI |
| 13 | B12 | RQVAQTLQADVLWQM | 61 | F12 | AIGNDGPLYGTLNNP |
| 14 | B11 | AQTLQADVLWQMGYT | 62 | F11 | NDGPLYGTLNNPADQ |
| 15 | B10 | LQADVLWQMGYTGAN | 63 | F10 | PLYGTLNNPADQMDV |
| 16 | B9 | DVLWQMGYTGANVRV | 64 | F9 | GTLNNPADQMDVIGV |
| 17 | B8 | WQMGYTGANVRVAVF | 65 | F8 | NNPADQMDVIGVGGI |
| 18 | B7 | GYTGANVRVAVFDTG | 66 | F7 | ADQMDVIGVGGIDFE |
| 19 | B6 | GANVRVAVFDTGLSE | 67 | F6 | MDVIGVGGIDFEDNI |
| 20 | B5 | VRVAVFDTGLSEKHP | 68 | F5 | IGVGGIDFEDNIARF |
| 21 | B4 | AVFDTGLSEKHPHFK | 69 | F4 | GGIDFEDNIARFSSR |
| 22 | B3 | DTGLSEKHPHFKNVK | 70 | F3 | DFEDNIARFSSRGMT |
| 23 | B2 | LSEKHPHFKNVKERT | 71 | F2 | DNIARFSSRGMTTWE |
| 24 | B1 | KHPHFKNVKERTNWT | 72 | F1 | ARFSSRGMTTWELPG |
| 25 | C12 | HFKNVKERTNWTNER | 73 | G12 | SSRGMTTWELPGGYG |
| 26 | C11 | NVKERTNWTNERTLD | 74 | G11 | GMTTWELPGGYGRMK |
| 27 | C10 | ERTNWTNERTLDDGL | 75 | G10 | TWELPGGYGRMKPDI |
| 28 | C9 | NWTNERTLDDGLGHG | 76 | G9 | LPGGYGRMKPDIVTY |
| 29 | C8 | NERTLDDGLGHGTFV | 77 | G8 | GYGRMKPDIVTYGAG |
| 30 | C7 | TLDDGLGHGTFVAGV | 78 | G7 | RMKPDIVTYGAGVRG |
| 31 | C6 | DGLGHGTFVAGVIAS | 79 | G6 | PDIVTYGAGVRGSGV |
| 32 | C5 | GHGTFVAGVIASMRE | 80 | G5 | VTYGAGVRGSGVKGG |
| 33 | C4 | TFVAGVIASMRECQG | 81 | G4 | GAGVRGSGVKGGCRA |
| 34 | C3 | AGVIASMRECQGFAP | 82 | G3 | VRGSGVKGGCRALSG |
| 35 | C2 | IASMRECQGFAPDAE | 83 | G2 | SGVKGGCRALSGTSV |
| 36 | C1 | MRECQGFAPDAELHI | 84 | G1 | KGGCRALSGTSVASP |
| 37 | D12 | CQGFAPDAELHIFRV | 85 | H12 | CRALSGTSVASPVVA |
| 38 | D11 | FAPDAELHIFRVFTN | 86 | H11 | LSGTSVASPVVAGAV |
| 39 | D10 | DAELHIFRVFTNNQV | 87 | H10 | TSVASPVVAGAVTLL |
| 40 | D9 | LHIFRVFTNNQVSYT | 88 | H9 | ASPVVAGAVTLLVST |
| 41 | D8 | FRVFTNNQVSYTSWF | 89 | H8 | VVAGAVTLLVSTVQK |
| 42 | D7 | FTNNQVSYTSWFLDA | 90 | H7 | GAVTLLVSTVQKREL |
| 43 | D6 | NQVSYTSWFLDAFNY | 91 | H6 | TLLVSTVQKRELVNP |
| 44 | D5 | SYTSWFLDAFNYAIL | 92 | H5 | VSTVQKRELVNPASM |
| 45 | D4 | SWFLDAFNYAILKKI | 93 | H4 | VQKRELVNPASMKQA |
| 46 | D3 | LDAFNYAILKKIDVL | 94 | H3 | RELVNPASMKQALIA |
| 47 | D2 | FNYAILKKIDVLNLS | 95 | H2 | VNPASMKQALIASAR |
| 48 | D1 | AILKKIDVLNLSIGG | 96 | H1 | ASMKQALIASARRLP |

FIG._6B

| | | |
|---|---|---|
| 97 | I12 | IKDFHVYFRESRDAG |
| 98 | I11 | DAELHIFRVFTNNQV |
| 99 | I10 | KQALIASARRLPGVN |
| 100 | I9 | LIASARRLPGVNMFE |
| 101 | I8 | SARRLPGVNMFEQGH |
| 102 | I7 | RLPGVNMFEQGHGKL |
| 103 | I6 | GVNMFEQGHGKLDLL |
| 104 | I5 | MFEQGHGKLDLLRAY |
| 105 | I4 | QGHGKLDLLRAYQIL |
| 106 | I3 | GKLDLLRAYQILNSY |
| 107 | I2 | DLLRAYQILNSYKPQ |
| 108 | I1 | RAYQILNSYKPQASL |
| 109 | J12 | QILNSYKPQASLSPS |
| 110 | J11 | NSYKPQASLSPSYID |
| 111 | J10 | KPQASLSPSYIDLTE |
| 112 | J9 | ASLSPSYIDLTECPY |
| 113 | J8 | SPSYIDLTECPYMWP |
| 114 | J7 | YIDLTECPYMWPYCS |
| 115 | J6 | LTECPYMWPYCSQPI |
| 116 | J5 | CPYMWPYCSQPIYYG |

FIG._6C

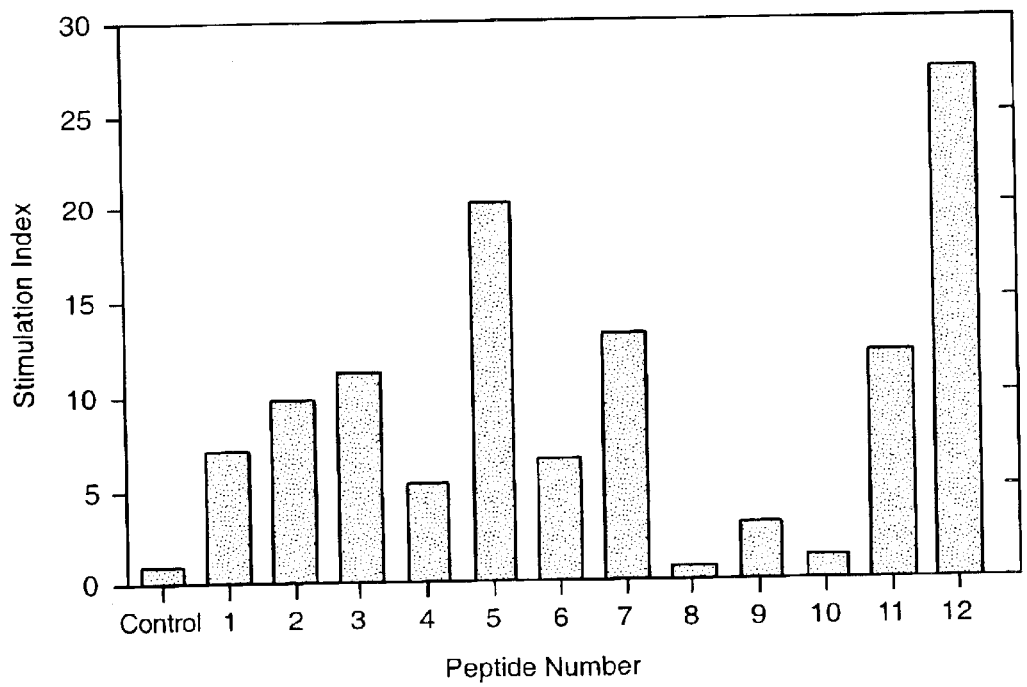

FIG._10

MKLVNIWLLLLVLLCGKKHLGDRLEKKSFEKAPCPGCSHLTLKVEFSSTVVEYEYIVAFNGYFT
AKARNSFISSALKSSEVDNWRIIPRNNPSSDYPSDFEVIQIKEKQKAGLLTLEDHPNIKRVTPQR
KVFRSLKYAESDPTVPCNETRWSQKWQSSRPLRRASLSGSGFWHATGRHSSRLLRAIPRQVAQ
TLQADVLWQMGYTGANVRVAVFDTGLSEKHPHFKNVKERTNWTNERTLDDGLGHGTFVAGVIASM
RECQGFAPDAELHIFRVFTNNQVSYTSWFLDAFNYAILKKIDVLNLSIGGPDFMDHPFVDKWEL
TANNVIMVSAIGNDGPLYGTLNNPADQMDVIGVGGIDFEDNIARFSSRGMTTWELPGGYGRMKPD
IVTYGAGVRGSGVKGGCRALSGTSVASPVVAGAVTLLVSTVQKRELVNPASMKQALIASARRLPG
VNMFEQGHGKLDLLRAYQILNSYKPQASLSPSYIDLTECPYMWPYCSQPIYYGGMPTVVNVTILN
GMGVTGRIVDKPDWQPYLPQNGDNIEVAFSYSSVLWPWSGYLAISISVTKKAASWEGIAQGHVMI
TVASPAETESKNGAEQTSTVKLPIKVKIIPTPPRSKRVLWDQYHNLRYPPGYFPRDNLRMKNDPL
DWNGDHIHTNFRDMYQHLRSMGYFVEVLGAPFTCFDASQYGTLLMVDSEEEYFPEEIAKLRRDVD
NGLSLVIFSDWYNTSVMRKVKFYDENTRQWWMPDTGGANIPALNELLSVWNMGFSDGLYEGEFTL
ANHDMYYASGCSIAKFPEDGVVITQTFKDQGLEVLKQETAVVENVPILGLYQIPAEGGGRIVLYG
DSNCLDDSHRQKDCFWLLDALLQYTSYGVTPPSLSHSGNRQRPPSGAGSVTPERMEGNHLHRYSK
VLEAHLGDPKPRPLPACPRLSWAKPQPLNETAPSNLMKHQKLLSIDLDKVVLPNFRSNRPQVRPL
SPGESGAWDIPGGIMPGRYNQEVGQTIPVFAFLGAMVLAFFVVQINKAKSRPKRRKPRVKRPQL
MQQVHPPKTPSV

```
                  10         20         30         40         50
BPN'       AQSVPYGVSQ-IKAPALHSQGYTGSNVKVAVIDSGIDSSHPDLK-VAGGA    48
SAVINASE   AQSVPWGISR-VQAPAAHNRGLTGSGVKVAVLDTGI-STHPDLN-IRGGA    47
S2HSBT     -RAIPRQVAQTLQADVLWQMGYTGANVRVAVFDTGLSEKHPHFKNVKERT    49

60         70         80         90        100
BPN'       SMVPSETNPFQDNNSHGTHVAGTVAALNNSIGVLGVAPSASLYAVKVLGA    98
SAVINASE   SFVPGEPST-QDGNGHGTHVAGTIAALNNSIGVLGVAPSAELYAVKVLGA    96
S2HSBT     NW--TNERTLDDGLGHGTFVAGVIASMRECQGF---APDAELHIFRVFTN    94

110        120        130        140        150
BPN'       DGSGQYSWIINGIEWAIANNMDVINMSLGGPS-GSAALKAAVDKAVASGV   147
SAVINASE   SGSGSVSSIAQGLEWAGNNGMHVANLSLGSPS-PSATLEQAVNSATSRGV   145
S2HSBT     NQVSYTSWFLDAFNYAILKKIDVLNLSIGGPDFMDHPFVDKVWELTANNV   144

160        170        180        190        200
BPN'       VVVAAAGNEGTSGSSSTVGYPGKYPSVIAVGAVDSSNQRASFSSVGPEL-   197
SAVINASE   LVVAASGNSGA---GSISYPARYANAMAVGATDQNNNRASFSQYGAGL-    191
S2HSBT     IMVSAIGNDGP--LYGTLNNPADQMDVIGVGGIDFEDNIARFSSRGMTTW   192

210        220        230        240        250
BPN'       ------DVMAPGVSIQSTLPGNKYGAYNGTSMASPHVAGAAALIL        235
SAVINASE   ------DIVAPGVNVQSTYPGSTYASLNGTSMATPHVAGAAALVK        229
S2HSBT     ELPGGYGRMKPDIVTYGAGVRGSGVKGGCRALSGTSVASPVVAGAVTLLV   242

260        270        280        290
BPN'       SKHPNWTNTQ---VRSSLENTTTKLGDSFYYGKGLINVQAAAQ          275
SAVINASE   QKNPSWSNVQ---IRNHLKNTATSLGSTNLYGSGLVNAEAATR          269
S2HSBT     STVQKRELVNPASMKQALIASARRLPGVNMFEQG----HGKL           280
```

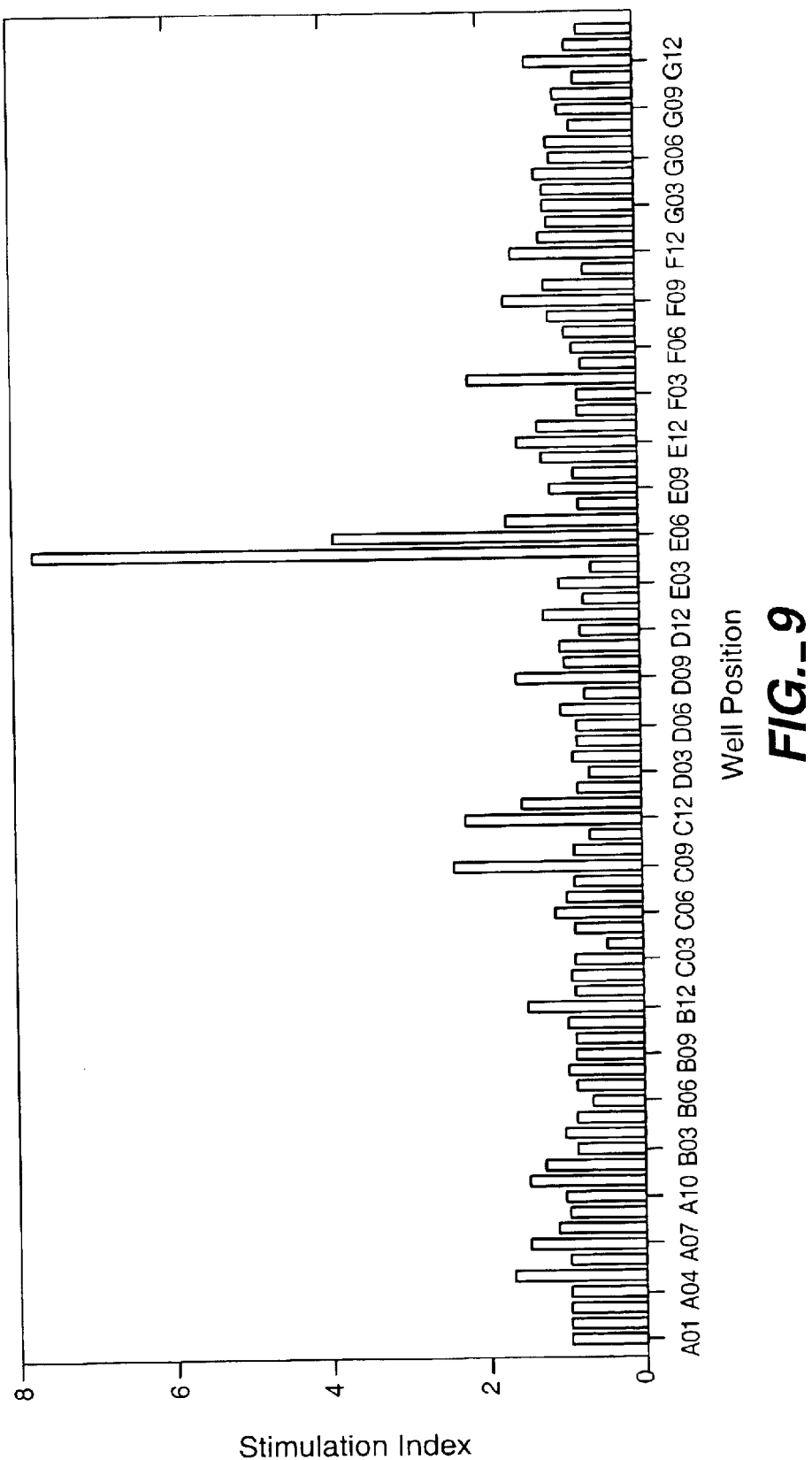
FIG._9

SEQUENCE LISTING

```
<160> NUMBER OF SEQ ID NOS: 211

<210> SEQ ID NO 1
<211> LENGTH: 1495
<212> TYPE: DNA
<213> ORGANISM: Bacillus amyloliquefaciens
<220> FEATURE:
<221> NAME/KEY: mat_peptide
<222> LOCATION: (417)..(1495)
<221> NAME/KEY: CDS
<222> LOCATION: (96)..(1244)
<221> NAME/KEY: misc_feature
<222> LOCATION: (96)..(98)
<223> OTHER INFORMATION: The nnn at positions 96 through 98 represents
      gtg, which is to code for methionine.
<221> NAME/KEY: misc_feature
<222> LOCATION: (582)..(584)
<223> OTHER INFORMATION: The nnn at positions 582 through 584 represents
      Xaa, which in a preferred embodiment (aat) is to
      code for asparagine, but which may  also code for
      proline.
<221> NAME/KEY: misc_feature
<222> LOCATION: (585)..(587)
<223> OTHER INFORMATION: The nnn at positions 585 through 587 represents
      Xaa, which in a preferred embodiment (cct) is to
      code for proline, but which may also code for
      asparagine.
<221> NAME/KEY: misc_feature
<222> LOCATION: (597)..(599)
<223> OTHER INFORMATION: The nnn at positions 597 to 599 represents Xaa,
      which in a preferred embodiment (aac) is to code
      for asparagine, but which may also code for
      aspartic acid.
```

```
<221> NAME/KEY: misc_feature
<222> LOCATION: (678)..(680)
<223> OTHER INFORMATION: The nnn at positions 678 through 680 represents
      Xaa, which in a preferred embodiment (gca) is to
      code for alanine, but which may also code for
      serine.
<221> NAME/KEY: misc_feature
<222> LOCATION: (681)..(683)
<223> OTHER INFORMATION: The nnn at positions 681 through 683 represents
      Xaa, which in a preferred embodiment (tca) is to
      code for serine, but which may also code for
      alanine.
<221> NAME/KEY: misc_feature
<222> LOCATION: (708)..(710)
<223> OTHER INFORMATION: The nnn at positions 708 through 710 represents
      Xaa, which in a preferred embodiment (gct) is to
      code for alanine, but which may also code for
      aspartic acid.
<221> NAME/KEY: misc_feature
<222> LOCATION: (711)..(713)
<223> OTHER INFORMATION: The nnn at positions 711 through 713 represents
      Xaa, which in a preferred embodiment (gac) is to
      code for aspartic acid, but which may also code
      for alanine.
<221> NAME/KEY: misc_feature
<222> LOCATION: (888)..(890)
<223> OTHER INFORMATION: The nnn at positions 888 through 890 represents
      Xaa, which in a preferred embodiment (act) is to
      code for threonine, but which may also code for
      serine.
<221> NAME/KEY: misc_feature
<222> LOCATION: (891)..(893)
<223> OTHER INFORMATION: The nnn at positions 891 through 893 represents
      Xaa, which in a preferred embodiment (tcc) is to
      code for serine, but which may also code for
      threonine.
<221> NAME/KEY: misc_feature
<222> LOCATION: (1167)..(1169)
<223> OTHER INFORMATION: The nnn at positions 1167 through 1169
      represents Xaa, which in a preferred embodiment (gaa) is to
      code for glutamic acid, but which may also code
      for glutamine.

<400> SEQUENCE: 1
ggtctactaa aatattattc catactatac aattaataca cagaataatc tgtctattgg        60
ttattctgca aatgaaaaaa aggagaggat aaaga nnn aga ggc aaa aaa gta          113
                                       Xaa Arg Gly Lys Lys Val
                                           -105 tgg atc agt ttg ctg ttt gct tta gcg tta atc ttt acg atg gcg ttc         161
Trp Ile Ser Leu Leu Phe Ala Leu Ala Leu Ile Phe Thr Met Ala Phe
    -100                 -95                 -90 ggc agc aca tcc tct gcc cag gcg gca ggg aaa tca aac ggg gaa aag         209
Gly Ser Thr Ser Ser Ala Gln Ala Ala Gly Lys Ser Asn Gly Glu Lys
-85                 -80                 -75                 -70 aaa tat att gtc ggg ttt aaa cag aca atg agc acg atg agc gcc gct         257
Lys Tyr Ile Val Gly Phe Lys Gln Thr Met Ser Thr Met Ser Ala Ala
                -65                 -60                 -55 aag aag aaa gat gtc att tct gaa aaa ggc ggg aaa gtg caa aag caa         305
Lys Lys Lys Asp Val Ile Ser Glu Lys Gly Gly Lys Val Gln Lys Gln
            -50                 -45                 -40 ttc aaa tat gta gac gca gct tca gct aca tta aac gaa aaa gct gta         353
Phe Lys Tyr Val Asp Ala Ala Ser Ala Thr Leu Asn Glu Lys Ala Val
        -35                 -30                 -25 aaa gaa ttg aaa aaa gac ccg agc gtc gct tac gtt gaa gaa gat cac         401
Lys Glu Leu Lys Lys Asp Pro Ser Val Ala Tyr Val Glu Glu Asp His
    -20                 -15                 -10 gta gca cat gcg tac gcg cag tcc gtg cct tac ggc gta tca caa att         449
Val Ala His Ala Tyr Ala Gln Ser Val Pro Tyr Gly Val Ser Gln Ile
-5              -1   1               5                  10
```

```
aaa gcc cct gct ctg cac tct caa ggc tac act gga tca aat gtt aaa      497
Lys Ala Pro Ala Leu His Ser Gln Gly Tyr Thr Gly Ser Asn Val Lys
            15                  20                  25 gta gcg gtt atc gac agc ggt atc gat tct tct cat cct gat tta aag      545
Val Ala Val Ile Asp Ser Gly Ile Asp Ser Ser His Pro Asp Leu Lys
        30                  35                  40 gta gca ggc gga gcc agc atg gtt cct tct gaa aca nnn nnn ttc caa      593
Val Ala Gly Gly Ala Ser Met Val Pro Ser Glu Thr Xaa Xaa Phe Gln
    45                  50                  55 gac nnn aac tct cac gga act cac gtt gcc ggc aca gtt gcg gct ctt      641
Asp Xaa Asn Ser His Gly Thr His Val Ala Gly Thr Val Ala Ala Leu
60                  65                  70                  75 aat aac tca atc ggt gta tta ggc gtt gcg cca agc nnn nnn ctt tac      689
Asn Asn Ser Ile Gly Val Leu Gly Val Ala Pro Ser Xaa Xaa Leu Tyr
            80                  85                  90 gct gta aaa gtt ctc ggt nnn nnn ggt tcc ggc caa tac agc tgg atc      737
Ala Val Lys Val Leu Gly Xaa Xaa Gly Ser Gly Gln Tyr Ser Trp Ile
        95                  100                 105 att aac gga atc gag tgg gcg atc gca aac aat atg gac gtt att aac      785
Ile Asn Gly Ile Glu Trp Ala Ile Ala Asn Asn Met Asp Val Ile Asn
    110                 115                 120 atg agc ctc ggc gga cct tct ggt tct gct gct tta aaa gcg gca gtt      833
Met Ser Leu Gly Gly Pro Ser Gly Ser Ala Ala Leu Lys Ala Ala Val
125                 130                 135 gat aaa gcc gtt gca tcc ggc gtc gta gtc gtt gcg gca gcc ggt aac      881
Asp Lys Ala Val Ala Ser Gly Val Val Val Ala Ala Ala Gly Asn
140                 145                 150                 155 gaa ggc nnn nnn ggc agc tca agc aca gtg ggc tac cct ggt aaa tac      929
Glu Gly Xaa Xaa Gly Ser Ser Ser Thr Val Gly Tyr Pro Gly Lys Tyr
            160                 165                 170 cct tct gtc att gca gta ggc gct gtt gac agc agc aac caa aga gca      977
Pro Ser Val Ile Ala Val Gly Ala Val Asp Ser Ser Asn Gln Arg Ala
        175                 180                 185 tct ttc tca agc gta gga cct gag ctt gat gtc atg gca cct ggc gta     1025
Ser Phe Ser Ser Val Gly Pro Glu Leu Asp Val Met Ala Pro Gly Val
    190                 195                 200 tct atc caa agc acg ctt cct gga aac aaa tac ggg gcg tac aac ggt     1073
Ser Ile Gln Ser Thr Leu Pro Gly Asn Lys Tyr Gly Ala Tyr Asn Gly
205                 210                 215 acg tca atg gca tct ccg cac gtt gcc gga gcg gct gct ttg att ctt     1121
Thr Ser Met Ala Ser Pro His Val Ala Gly Ala Ala Ala Leu Ile Leu
220                 225                 230                 235 tct aag cac ccg aac tgg aca aac act caa gtc cgc agc agt tta nnn     1169
Ser Lys His Pro Asn Trp Thr Asn Thr Gln Val Arg Ser Ser Leu Xaa
            240                 245                 250 aac acc act aca aaa ctt ggt gat tct ttc tac tat gga aaa ggg ctg     1217
Asn Thr Thr Thr Lys Leu Gly Asp Ser Phe Tyr Tyr Gly Lys Gly Leu
        255                 260                 265 atc aac gta cag gcg gca gct cag taa aacataaaaa accggccttg           1264
Ile Asn Val Gln Ala Ala Ala Gln
    270                 275 gccccgccgg ttttttatt tttcttcctc cgcatgttca atccgctcca taatcgacgg    1324
atggctccct ctgaaaattt taacgagaaa cggcgggttg acccggctca gtcccgtaac   1384
ggccaagtcc tgaaacgtct caatcgccgc ttcccggttt ccgtcagct caatgccgta    1444 acggtcggcg gcgttttcct gataccggga gacggcattc gtaatcggat c            1495

<210> SEQ ID NO 2
<211> LENGTH: 382
```

```
<212> TYPE: PRT
<213> ORGANISM: Bacillus amyloliquefaciens
<220> FEATURE:
<221> NAME/KEY: VARIANT
<222> LOCATION: (1)...(382)
<223> OTHER INFORMATION: Xaa = Any Amino Acid

<400> SEQUENCE: 2

Xaa Arg Gly Lys Lys Val Trp Ile Ser Leu Leu Phe Ala Leu Ala Leu
 1               5                  10                  15

Ile Phe Thr Met Ala Phe Gly Ser Thr Ser Ala Gln Ala Ala Gly
            20                  25                  30

Lys Ser Asn Gly Glu Lys Lys Tyr Ile Val Gly Phe Lys Gln Thr Met
             35                  40                  45

Ser Thr Met Ser Ala Ala Lys Lys Lys Asp Val Ile Ser Glu Lys Gly
     50                  55                  60

Gly Lys Val Gln Lys Gln Phe Lys Tyr Val Asp Ala Ala Ser Ala Thr
 65                  70                  75                  80

Leu Asn Glu Lys Ala Val Lys Glu Leu Lys Lys Asp Pro Ser Val Ala
                 85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
            115                 120                 125

Thr Gly Ser Asn Val Lys Val Ala Val Ile Asp Ser Gly Ile Asp Ser
130                 135                 140

Ser His Pro Asp Leu Lys Val Ala Gly Gly Ala Ser Met Val Pro Ser
145                 150                 155                 160

Glu Thr Xaa Xaa Phe Gln Asp Xaa Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Xaa Xaa Leu Tyr Ala Val Lys Val Leu Gly Xaa Xaa Gly Ser
            195                 200                 205

Gly Gln Tyr Ser Trp Ile Ile Asn Gly Ile Glu Trp Ala Ile Ala Asn
210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
            245                 250                 255

Val Ala Ala Ala Gly Asn Glu Gly Xaa Xaa Gly Ser Ser Ser Thr Val
            260                 265                 270

Gly Tyr Pro Gly Lys Tyr Pro Ser Val Ile Ala Val Gly Ala Val Asp
            275                 280                 285

Ser Ser Asn Gln Arg Ala Ser Phe Ser Ser Val Gly Pro Glu Leu Asp
290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
            325                 330                 335

Ala Ala Ala Leu Ile Leu Ser Lys His Pro Asn Trp Thr Asn Thr Gln
            340                 345                 350

Val Arg Ser Ser Leu Xaa Asn Thr Thr Thr Lys Leu Gly Asp Ser Phe
            355                 360                 365

Tyr Tyr Gly Lys Gly Leu Ile Asn Val Gln Ala Ala Ala Gln
```

```
                 370                 375                 380

<210> SEQ ID NO 3
<211> LENGTH: 275
<212> TYPE: PRT
<213> ORGANISM: Bacillus amyloliquefaciens

<400> SEQUENCE: 3

Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 4
<211> LENGTH: 275
<212> TYPE: PRT
<213> ORGANISM: Bacillus subtilis

<400> SEQUENCE: 4

Ala Gln Ser Val Pro Tyr Gly Ile Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
```

```
              35                  40                  45
Ser Phe Val Pro Ser Glu Thr Asn Pro Tyr Gln Asp Gly Ser Ser His
     50                  55                  60

Gly Thr His Val Ala Gly Thr Ile Ala Ala Leu Asn Asn Ser Ile Gly
 65                  70                  75                  80

Val Leu Gly Val Ser Pro Ser Ala Ser Leu Tyr Ala Val Lys Val Leu
                 85                  90                  95

Asp Ser Thr Gly Ser Gly Gln Tyr Ser Trp Ile Ile Asn Gly Ile Glu
             100                 105                 110

Trp Ala Ile Ser Asn Asn Met Asp Val Ile Asn Met Ser Leu Gly Gly
         115                 120                 125

Pro Thr Gly Ser Thr Ala Leu Lys Thr Val Val Asp Lys Ala Val Ser
130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                 165                 170                 175

Val Gly Ala Val Asn Ser Ser Asn Gln Arg Ala Ser Phe Ser Ser Ala
             180                 185                 190

Gly Ser Glu Leu Asp Val Met Ala Pro Gly Val Ser Ile Gln Ser Thr
         195                 200                 205

Leu Pro Gly Gly Thr Tyr Gly Ala Tyr Asn Gly Thr Ser Met Ala Thr
210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                 245                 250                 255

Leu Gly Asn Ser Phe Tyr Tyr Gly Lys Gly Leu Ile Asn Val Gln Ala
             260                 265                 270

Ala Ala Gln
        275

<210> SEQ ID NO 5
<211> LENGTH: 274
<212> TYPE: PRT
<213> ORGANISM: Bacillus licheniformis

<400> SEQUENCE: 5

Ala Gln Thr Val Pro Tyr Gly Ile Pro Leu Ile Lys Ala Asp Lys Val
 1                5                  10                  15

Gln Ala Gln Gly Phe Lys Gly Ala Asn Val Lys Val Ala Val Leu Asp
                 20                  25                  30

Thr Gly Ile Gln Ala Ser His Pro Asp Leu Asn Val Gly Gly Ala
             35                  40                  45

Ser Phe Val Ala Gly Glu Ala Tyr Asn Thr Asp Gly Asn Gly His Gly
     50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
             100                 105                 110

Ala Thr Thr Asn Gly Met Asp Val Ile Asn Met Ser Leu Gly Gly Ala
         115                 120                 125
```

```
Ser Gly Ser Thr Ala Met Lys Gln Ala Val Asp Asn Ala Tyr Ala Arg
        130                 135                 140

Gly Val Val Val Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
210                 215                 220

His Val Ala Gly Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220
```

-continued

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 7

Ile Lys Asp Phe His Val Tyr Phe Arg Glu Ser Arg Asp Ala Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 8

Leu Glu Gln Ala Val Asn Ser Ala Thr Ser Arg Gly Val Leu Val
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 9

Ala Gln Ser Val Pro Trp Gly Ile Ser Arg Val Gln Ala Pro Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 10

Val Pro Trp Gly Ile Ser Arg Val Gln Ala Pro Ala Ala His Asn
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 11

Gly Ile Ser Arg Val Gln Ala Pro Ala Ala His Asn Arg Gly Leu
1               5                   10                  15

<210> SEQ ID NO 12
<211> LENGTH: 15
<212> TYPE: PRT
<213> ORGANISM: Artificial Sequence
```

-continued

```
<220> FEATURE:
<223> OTHER INFORMATION: Description of Artificial Sequence: Synthetic

<400> SEQUENCE: 12

Arg Val Gln Ala Pro Ala Ala His Asn Arg Gly Leu Thr Gly Ser
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 13

Ala Pro Ala Ala His Asn Arg Gly Leu Thr Gly Ser Gly Val Lys
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 14

Ala His Asn Arg Gly Leu Thr Gly Ser Gly Val Lys Val Ala Val
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 15

Arg Gly Leu Thr Gly Ser Gly Val Lys Val Ala Val Leu Asp Thr
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 16

Thr Gly Ser Gly Val Lys Val Ala Val Leu Asp Thr Gly Ile Ser
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 17

Gly Val Lys Val Ala Val Leu Asp Thr Gly Ile Ser Thr His Pro
 1               5                  10                  15

<210> SEQ ID NO 18
<211> LENGTH: 15
<212> TYPE: PRT
<213> ORGANISM: Artificial Sequence
<220> FEATURE:
```

<223> OTHER INFORMATION: Description of Artificial Sequence: Synthetic

<400> SEQUENCE: 18

Val Ala Val Leu Asp Thr Gly Ile Ser Thr His Pro Asp Leu Asn
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 19

Leu Asp Thr Gly Ile Ser Thr His Pro Asp Leu Asn Ile Arg Gly
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 20

Gly Ile Ser Thr His Pro Asp Leu Asn Ile Arg Gly Gly Ala Ser
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 21

Thr His Pro Asp Leu Asn Ile Arg Gly Gly Ala Ser Phe Val Pro
 1               5                  10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 22

Asp Leu Asn Ile Arg Gly Gly Ala Ser Phe Val Pro Gly Glu Pro
 1               5                  10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 23

Ile Arg Gly Gly Ala Ser Phe Val Pro Gly Glu Pro Ser Thr Gln
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic

```
<400> SEQUENCE: 24

Gly Ala Ser Phe Val Pro Gly Glu Pro Ser Thr Gln Asp Gly Asn
 1               5                  10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 25

Phe Val Pro Gly Glu Pro Ser Thr Gln Asp Gly Asn Gly His Gly
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 26

Gly Glu Pro Ser Thr Gln Asp Gly Asn Gly His Gly Thr His Val
 1               5                  10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 27

Ser Thr Gln Asp Gly Asn Gly His Gly Thr His Val Ala Gly Thr
 1               5                  10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 28

Asp Gly Asn Gly His Gly Thr His Val Ala Gly Thr Ile Ala Ala
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 29

Gly His Gly Thr His Val Ala Gly Thr Ile Ala Ala Leu Asn Asn
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
<400> SEQUENCE: 30

Thr His Val Ala Gly Thr Ile Ala Ala Leu Asn Asn Ser Ile Gly
  1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 31

Ala Gly Thr Ile Ala Ala Leu Asn Asn Ser Ile Gly Val Leu Gly
  1               5                  10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 32

Ile Ala Ala Leu Asn Asn Ser Ile Gly Val Leu Gly Val Ala Pro
  1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 33

Leu Asn Asn Ser Ile Gly Val Leu Gly Val Ala Pro Ser Ala Glu
  1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 34

Ser Ile Gly Val Leu Gly Val Ala Pro Ser Ala Glu Leu Tyr Ala
  1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 35

Val Leu Gly Val Ala Pro Ser Ala Glu Leu Tyr Ala Val Lys Val
  1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 36
```

```
Val Ala Pro Ser Ala Glu Leu Tyr Ala Val Lys Val Leu Gly Ala
 1               5                  10                  15
```

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 37

```
Ser Ala Glu Leu Tyr Ala Val Lys Val Leu Gly Ala Ser Gly Ser
 1               5                  10                  15
```

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 38

```
Leu Tyr Ala Val Lys Val Leu Gly Ala Ser Gly Ser Gly Ser Val
 1               5                  10                  15
```

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 39

```
Val Lys Val Leu Gly Ala Ser Gly Ser Gly Ser Val Ser Ser Ile
 1               5                  10                  15
```

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 40

```
Leu Gly Ala Ser Gly Ser Gly Ser Val Ser Ser Ile Ala Gln Gly
 1               5                  10                  15
```

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 41

```
Ser Gly Ser Gly Ser Val Ser Ser Ile Ala Gln Gly Leu Glu Trp
 1               5                  10                  15
```

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 42

-continued

```
Gly Ser Val Ser Ser Ile Ala Gln Gly Leu Glu Trp Ala Gly Asn
1               5                   10                  15
```

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 43

```
Ser Ser Ile Ala Gln Gly Leu Glu Trp Ala Gly Asn Asn Gly Met
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 44

```
Ala Gln Gly Leu Glu Trp Ala Gly Asn Asn Gly Met His Val Ala
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 45

```
Leu Glu Trp Ala Gly Asn Asn Gly Met His Val Ala Asn Leu Ser
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 46

```
Ala Gly Asn Asn Gly Met His Val Ala Asn Leu Ser Leu Gly Ser
1               5                   10                  15
```

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 47

```
Asn Gly Met His Val Ala Asn Leu Ser Leu Gly Ser Pro Ser Pro
1               5                   10                  15
```

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 48

```
His Val Ala Asn Leu Ser Leu Gly Ser Pro Ser Pro Ser Ala Thr
```

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 49

Asn Leu Ser Leu Gly Ser Pro Ser Pro Ser Ala Thr Leu Glu Gln
 1               5                  10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 50

Leu Gly Ser Pro Ser Pro Ser Ala Thr Leu Glu Gln Ala Val Asn
 1               5                  10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 51

Pro Ser Pro Ser Ala Thr Leu Glu Gln Ala Val Asn Ser Ala Thr
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 52

Ser Ala Thr Leu Glu Gln Ala Val Asn Ser Ala Thr Ser Arg Gly
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 53

Leu Glu Gln Ala Val Asn Ser Ala Thr Ser Arg Gly Val Leu Val
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 54

Ala Val Asn Ser Ala Thr Ser Arg Gly Val Leu Val Val Ala Ala
 1               5                  10                  15

```
<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 55

Ser Ala Thr Ser Arg Gly Val Leu Val Val Ala Ala Ser Gly Asn
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 56

Ser Arg Gly Val Leu Val Val Ala Ala Ser Gly Asn Ser Gly Ala
 1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 57

Val Leu Val Val Ala Ala Ser Gly Asn Ser Gly Ala Gly Ser Ile
 1               5                  10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 58

Val Ala Ala Ser Gly Asn Ser Gly Ala Gly Ser Ile Ser Tyr Pro
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 59

Ser Gly Asn Ser Gly Ala Gly Ser Ile Ser Tyr Pro Ala Arg Tyr
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 60

Ser Gly Ala Gly Ser Ile Ser Tyr Pro Ala Arg Tyr Ala Asn Ala
 1               5                  10                  15
```

```
<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 61

Gly Ser Ile Ser Tyr Pro Ala Arg Tyr Ala Asn Ala Met Ala Val
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 62

Ser Tyr Pro Ala Arg Tyr Ala Asn Ala Met Ala Val Gly Ala Thr
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 63

Ala Arg Tyr Ala Asn Ala Met Ala Val Gly Ala Thr Asp Gln Asn
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 64

Ala Asn Ala Met Ala Val Gly Ala Thr Asp Gln Asn Asn Asn Arg
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 65

Met Ala Val Gly Ala Thr Asp Gln Asn Asn Asn Arg Ala Ser Phe
 1               5                  10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 66

Gly Ala Thr Asp Gln Asn Asn Asn Arg Ala Ser Phe Ser Gln Tyr
 1               5                  10                  15
```

```
<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 67

Asp Gln Asn Asn Asn Arg Ala Ser Phe Ser Gln Tyr Gly Ala Gly
 1               5                  10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 68

Asn Asn Arg Ala Ser Phe Ser Gln Tyr Gly Ala Gly Leu Asp Ile
 1               5                  10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 69

Ala Ser Phe Ser Gln Tyr Gly Ala Gly Leu Asp Ile Val Ala Pro
 1               5                  10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 70

Ser Gln Tyr Gly Ala Gly Leu Asp Ile Val Ala Pro Gly Val Asn
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 71

Gly Ala Gly Leu Asp Ile Val Ala Pro Gly Val Asn Val Gln Ser
 1               5                  10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 72

Leu Asp Ile Val Ala Pro Gly Val Asn Val Gln Ser Thr Tyr Pro
 1               5                  10                  15

<210> SEQ ID NO 73
```

```
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 73

Val Ala Pro Gly Val Asn Val Gln Ser Thr Tyr Pro Gly Ser Thr
 1               5                  10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 74

Gly Val Asn Val Gln Ser Thr Tyr Pro Gly Ser Thr Tyr Ala Ser
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 75

Val Gln Ser Thr Tyr Pro Gly Ser Thr Tyr Ala Ser Leu Asn Gly
 1               5                  10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 76

Thr Tyr Pro Gly Ser Thr Tyr Ala Ser Leu Asn Gly Thr Ser Met
 1               5                  10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 77

Gly Ser Thr Tyr Ala Ser Leu Asn Gly Thr Ser Met Ala Thr Pro
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 78

Tyr Ala Ser Leu Asn Gly Thr Ser Met Ala Thr Pro His Val Ala
 1               5                  10                  15

<210> SEQ ID NO 79
<211> LENGTH: 15
```

-continued

```
<212> TYPE: PRT
<213> ORGANISM: Artificial Sequence
<220> FEATURE:
<223> OTHER INFORMATION: Description of Artificial Sequence: Synthetic

<400> SEQUENCE: 79

Leu Asn Gly Thr Ser Met Ala Thr Pro His Val Ala Gly Ala Ala
 1               5                  10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 80

Thr Ser Met Ala Thr Pro His Val Ala Gly Ala Ala Ala Leu Val
 1               5                  10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 81

Ala Thr Pro His Val Ala Gly Ala Ala Ala Leu Val Lys Gln Lys
 1               5                  10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 82

His Val Ala Gly Ala Ala Ala Leu Val Lys Gln Lys Asn Pro Ser
 1               5                  10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 83

Gly Ala Ala Ala Leu Val Lys Gln Lys Asn Pro Ser Trp Ser Asn
 1               5                  10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 84

Ala Leu Val Lys Gln Lys Asn Pro Ser Trp Ser Asn Val Gln Ile
 1               5                  10                  15

<210> SEQ ID NO 85
<211> LENGTH: 15
<212> TYPE: PRT
```

```
<213> ORGANISM: Artificial Sequence
<220> FEATURE:
<223> OTHER INFORMATION: Description of Artificial Sequence: Synthetic

<400> SEQUENCE: 85

Lys Gln Lys Asn Pro Ser Trp Ser Val Asn Gln Ile Arg Asn His
 1               5                  10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 86

Asn Pro Ser Trp Ser Asn Val Gln Ile Arg Asn His Leu Lys Asn
 1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 87

Trp Ser Asn Val Gln Ile Arg Asn His Leu Lys Asn Thr Ala Thr
 1               5                  10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 88

Val Gln Ile Arg Asn His Leu Lys Asn Thr Ala Thr Ser Leu Gly
 1               5                  10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 89

Arg Asn His Leu Lys Asn Thr Ala Thr Ser Leu Gly Ser Thr Asn
 1               5                  10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 90

Leu Lys Asn Thr Ala Thr Ser Leu Gly Ser Thr Asn Leu Tyr Gly
 1               5                  10                  15

<210> SEQ ID NO 91
<211> LENGTH: 15
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 91

Thr Ala Thr Ser Leu Gly Ser Thr Asn Leu Tyr Gly Ser Gly Leu
 1               5                  10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 92

Ser Leu Gly Ser Thr Asn Leu Tyr Gly Ser Gly Leu Val Asn Ala
 1               5                  10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 93

Ser Thr Asn Leu Tyr Gly Ser Gly Leu Val Asn Ala Glu Ala Ala
 1               5                  10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 94

Asn Leu Tyr Gly Ser Gly Leu Val Asn Ala Glu Ala Ala Thr Arg
 1               5                  10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 95

Asp Ala Glu Leu His Ile Phe Arg Val Phe Thr Asn Asn Gln Val
 1               5                  10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 96

Pro Leu Arg Arg Ala Ser Leu Ser Leu Gly Ser Gly Phe Trp His
 1               5                  10                  15

<210> SEQ ID NO 97
<211> LENGTH: 15
<212> TYPE: PRT
<213> ORGANISM: Artificial Sequence
<220> FEATURE:
```

<223> OTHER INFORMATION: Description of Artificial Sequence: Synthetic

<400> SEQUENCE: 97

Arg Ala Ser Leu Ser Leu Gly Ser Gly Phe Trp His Ala Thr Gly
 1               5                  10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 98

Leu Ser Leu Gly Ser Gly Phe Trp His Ala Thr Gly Arg His Ser
 1               5                  10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 99

Gly Ser Gly Phe Trp His Ala Thr Gly Arg His Ser Ser Arg Arg
 1               5                  10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 100

Phe Trp His Ala Thr Gly Arg His Ser Ser Arg Arg Leu Leu Arg
 1               5                  10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 101

Ala Thr Gly Arg His Ser Ser Arg Arg Leu Leu Arg Ala Ile Pro
 1               5                  10                  15

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 102

Arg His Ser Ser Arg Arg Leu Leu Arg Ala Ile Pro Arg Gln Val
 1               5                  10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic

```
<400> SEQUENCE: 103

Ser Arg Arg Leu Leu Arg Ala Ile Pro Arg Gln Val Ala Gln Thr
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 104

Leu Leu Arg Ala Ile Pro Arg Gln Val Ala Gln Thr Leu Gln Ala
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 105

Ala Ile Pro Arg Gln Val Ala Gln Thr Leu Gln Ala Asp Val Leu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 106

Arg Gln Val Ala Gln Thr Leu Gln Ala Asp Val Leu Trp Gln Met
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 107

Ala Gln Thr Leu Gln Ala Asp Val Leu Trp Gln Met Gly Tyr Thr
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 108

Leu Gln Ala Asp Val Leu Trp Gln Met Gly Tyr Thr Gly Ala Asn
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
```

<400> SEQUENCE: 109

Asp Val Leu Trp Gln Met Gly Tyr Thr Gly Ala Asn Val Arg Val
 1               5                  10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 110

Trp Gln Met Gly Tyr Thr Gly Ala Asn Val Arg Val Ala Val Phe
 1               5                  10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 111

Gly Tyr Thr Gly Ala Asn Val Arg Val Ala Val Phe Asp Thr Gly
 1               5                  10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 112

Gly Ala Asn Val Arg Val Ala Val Phe Asp Thr Gly Leu Ser Glu
 1               5                  10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 113

Val Arg Val Ala Val Phe Asp Thr Gly Leu Ser Glu Lys His Pro
 1               5                  10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 114

Ala Val Phe Asp Thr Gly Leu Ser Glu Lys His Pro His Phe Lys
 1               5                  10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 115

```
Asp Thr Gly Leu Ser Glu Lys His Pro His Phe Lys Asn Val Lys
 1               5                  10                  15
```

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 116

```
Leu Ser Glu Lys His Pro His Phe Lys Asn Val Lys Glu Arg Thr
 1               5                  10                  15
```

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 117

```
Lys His Pro His Phe Lys Asn Val Lys Glu Arg Thr Asn Trp Thr
 1               5                  10                  15
```

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 118

```
His Phe Lys Asn Val Lys Glu Arg Thr Asn Trp Thr Asn Glu Arg
 1               5                  10                  15
```

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 119

```
Asn Val Lys Glu Arg Thr Asn Trp Thr Asn Glu Arg Thr Leu Asp
 1               5                  10                  15
```

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 120

```
Glu Arg Thr Asn Trp Thr Asn Glu Arg Thr Leu Asp Asp Gly Leu
 1               5                  10                  15
```

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 121

```
Asn Trp Thr Asn Glu Arg Thr Leu Asp Asp Gly Leu Gly His Gly
 1               5                  10                  15
```

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 122

```
Asn Glu Arg Thr Leu Asp Asp Gly Leu Gly His Gly Thr Phe Val
 1               5                  10                  15
```

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 123

```
Thr Leu Asp Asp Gly Leu Gly His Gly Thr Phe Val Ala Gly Val
 1               5                  10                  15
```

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 124

```
Asp Gly Leu Gly His Gly Thr Phe Val Ala Gly Val Ile Ala Ser
 1               5                  10                  15
```

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 125

```
Gly His Gly Thr Phe Val Ala Gly Val Ile Ala Ser Met Arg Glu
 1               5                  10                  15
```

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 126

```
Thr Phe Val Ala Gly Val Ile Ala Ser Met Arg Glu Cys Gln Gly
 1               5                  10                  15
```

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 127

```
Ala Gly Val Ile Ala Ser Met Arg Glu Cys Gln Gly Phe Ala Pro
```

```
<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 128

Ile Ala Ser Met Arg Glu Cys Gln Gly Phe Ala Pro Asp Ala Glu
 1               5                  10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 129

Met Arg Glu Cys Gln Gly Phe Ala Pro Asp Ala Glu Leu His Ile
 1               5                  10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 130

Cys Gln Gly Phe Ala Pro Asp Ala Glu Leu His Ile Phe Arg Val
 1               5                  10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 131

Phe Ala Pro Asp Ala Glu Leu His Ile Phe Arg Val Phe Thr Asn
 1               5                  10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 132

Asp Ala Glu Leu His Ile Phe Arg Val Phe Thr Asn Asn Gln Val
 1               5                  10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 133

Leu His Ile Phe Arg Val Phe Thr Asn Asn Gln Val Ser Tyr Thr
 1               5                  10                  15
```

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 134

Phe Arg Val Phe Thr Asn Asn Gln Val Ser Tyr Thr Ser Trp Phe
 1               5                  10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 135

Phe Thr Asn Asn Gln Val Ser Tyr Thr Ser Trp Phe Leu Asp Ala
 1               5                  10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 136

Asn Gln Val Ser Tyr Thr Ser Trp Phe Leu Asp Ala Phe Asn Tyr
 1               5                  10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 137

Ser Tyr Thr Ser Trp Phe Leu Asp Ala Phe Asn Tyr Ala Ile Leu
 1               5                  10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 138

Ser Trp Phe Leu Asp Ala Phe Asn Tyr Ala Ile Leu Lys Lys Ile
 1               5                  10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 139

Leu Asp Ala Phe Asn Tyr Ala Ile Leu Lys Lys Ile Asp Val Leu
 1               5                  10                  15

```
<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 140

Phe Asn Tyr Ala Ile Leu Lys Lys Ile Asp Val Leu Asn Leu Ser
 1               5                  10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 141

Ala Ile Leu Lys Lys Ile Asp Val Leu Asn Leu Ser Ile Gly Gly
 1               5                  10                  15

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 142

Lys Lys Ile Asp Val Leu Asn Leu Ser Ile Gly Gly Pro Asp Phe
 1               5                  10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 143

Asp Val Leu Asn Leu Ser Ile Gly Gly Pro Asp Phe Met Asp His
 1               5                  10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 144

Asn Leu Ser Ile Gly Gly Pro Asp Phe Met Asp His Pro Phe Val
 1               5                  10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 145

Ile Gly Gly Pro Asp Phe Met Asp His Pro Phe Val Asp Lys Val
 1               5                  10                  15
```

```
<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 146

Pro Asp Phe Met Asp His Pro Phe Val Asp Lys Val Trp Glu Leu
 1               5                  10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 147

Met Asp His Pro Phe Val Asp Lys Val Trp Glu Leu Thr Ala Asn
 1               5                  10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 148

Pro Phe Val Asp Lys Val Trp Glu Leu Thr Ala Asn Asn Val Ile
 1               5                  10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 149

Asp Lys Val Trp Glu Leu Thr Ala Asn Asn Val Ile Met Val Ser
 1               5                  10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 150

Trp Glu Leu Thr Ala Asn Asn Val Ile Met Val Ser Ala Ile Gly
 1               5                  10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 151

Thr Ala Asn Asn Val Ile Met Val Ser Ala Ile Gly Asn Asp Gly
 1               5                  10                  15

<210> SEQ ID NO 152
```

-continued

```
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 152

Asn Val Ile Met Val Ser Ala Ile Gly Asn Asp Gly Pro Leu Tyr
 1               5                  10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 153

Met Val Ser Ala Ile Gly Asn Asp Gly Pro Leu Tyr Gly Thr Ile
 1               5                  10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 154

Ala Ile Gly Asn Asp Gly Pro Leu Tyr Gly Thr Leu Asn Asn Pro
 1               5                  10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 155

Asn Asp Gly Pro Leu Tyr Gly Thr Leu Asn Asn Pro Ala Asp Gln
 1               5                  10                  15

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 156

Pro Leu Tyr Gly Thr Leu Asn Asn Pro Ala Asp Gln Met Asp Val
 1               5                  10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 157

Gly Thr Leu Asn Asn Pro Ala Asp Gln Met Asp Val Ile Gly Val
 1               5                  10                  15

<210> SEQ ID NO 158
<211> LENGTH: 15
```

<212> TYPE: PRT
<213> ORGANISM: Artificial Sequence
<220> FEATURE:
<223> OTHER INFORMATION: Description of Artificial Sequence: Synthetic

<400> SEQUENCE: 158

Asn Asn Pro Ala Asp Gln Met Asp Val Ile Gly Val Gly Gly Ile
 1               5                  10                  15

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 159

Ala Asp Gln Met Asp Val Ile Gly Val Gly Gly Ile Asp Phe Glu
 1               5                  10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 160

Met Asp Val Ile Gly Val Gly Gly Ile Asp Phe Glu Asp Asn Ile
 1               5                  10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 161

Ile Gly Val Gly Gly Ile Asp Phe Glu Asp Asn Ile Ala Arg Phe
 1               5                  10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 162

Gly Gly Ile Asp Phe Glu Asp Asn Ile Ala Arg Phe Ser Ser Arg
 1               5                  10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 163

Asp Phe Glu Asp Asn Ile Ala Arg Phe Ser Ser Arg Gly Met Thr
 1               5                  10                  15

<210> SEQ ID NO 164
<211> LENGTH: 15
<212> TYPE: PRT

```
<213> ORGANISM: Artificial Sequence
<220> FEATURE:
<223> OTHER INFORMATION: Description of Artificial Sequence: Synthetic

<400> SEQUENCE: 164

Asp Asn Ile Ala Arg Phe Ser Ser Arg Gly Met Thr Thr Trp Glu
 1               5                  10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 165

Ala Arg Phe Ser Ser Arg Gly Met Thr Thr Trp Glu Leu Pro Gly
 1               5                  10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 166

Ser Ser Arg Gly Met Thr Thr Trp Glu Leu Pro Gly Gly Tyr Gly
 1               5                  10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 167

Gly Met Thr Thr Trp Glu Leu Pro Gly Gly Tyr Gly Arg Met Lys
 1               5                  10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 168

Thr Trp Glu Leu Pro Gly Gly Tyr Gly Arg Met Lys Pro Asp Ile
 1               5                  10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 169

Leu Pro Gly Gly Tyr Gly Arg Met Lys Pro Asp Ile Val Thr Tyr
 1               5                  10                  15

<210> SEQ ID NO 170
<211> LENGTH: 15
<212> TYPE: PRT
<213> ORGANISM: Artificial Sequence
```

```
<220> FEATURE:
<223> OTHER INFORMATION: Description of Artificial Sequence: Synthetic

<400> SEQUENCE: 170

Gly Tyr Gly Arg Met Lys Pro Asp Ile Val Thr Tyr Gly Ala Gly
 1               5                  10                  15

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 171

Arg Met Lys Pro Asp Ile Val Thr Tyr Gly Ala Gly Val Arg Gly
 1               5                  10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 172

Pro Asp Ile Val Thr Tyr Gly Ala Gly Val Arg Gly Ser Gly Val
 1               5                  10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 173

Val Thr Tyr Gly Ala Gly Val Arg Gly Ser Gly Val Lys Gly Gly
 1               5                  10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 174

Gly Ala Gly Val Arg Gly Ser Gly Val Lys Gly Gly Cys Arg Ala
 1               5                  10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 175

Val Arg Gly Ser Gly Val Lys Gly Gly Cys Arg Ala Leu Ser Gly
 1               5                  10                  15

<210> SEQ ID NO 176
<211> LENGTH: 15
<212> TYPE: PRT
<213> ORGANISM: Artificial Sequence
<220> FEATURE:
```

```
<223> OTHER INFORMATION: Description of Artificial Sequence: Synthetic

<400> SEQUENCE: 176

Ser Gly Val Lys Gly Gly Cys Arg Ala Leu Ser Gly Thr Ser Val
 1               5                  10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 177

Lys Gly Gly Cys Arg Ala Leu Ser Gly Thr Ser Val Ala Ser Pro
 1               5                  10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 178

Cys Arg Ala Leu Ser Gly Thr Ser Val Ala Ser Pro Val Val Ala
 1               5                  10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 179

Leu Ser Gly Thr Ser Val Ala Ser Pro Val Val Ala Gly Ala Val
 1               5                  10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 180

Thr Ser Val Ala Ser Pro Val Val Ala Gly Ala Val Thr Leu Leu
 1               5                  10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 181

Ala Ser Pro Val Val Ala Gly Ala Val Thr Leu Leu Val Ser Thr
 1               5                  10                  15

<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
```

<400> SEQUENCE: 182

Val Val Ala Gly Ala Val Thr Leu Leu Val Ser Thr Val Gln Lys
 1               5                  10                  15

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 183

Gly Ala Val Thr Leu Leu Val Ser Thr Val Gln Lys Arg Glu Leu
 1               5                  10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 184

Thr Leu Leu Val Ser Thr Val Gln Lys Arg Glu Leu Val Asn Pro
 1               5                  10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 185

Val Ser Thr Val Gln Lys Arg Glu Leu Val Asn Pro Ala Ser Met
 1               5                  10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 186

Val Gln Lys Arg Glu Leu Val Asn Pro Ala Ser Met Lys Gln Ala
 1               5                  10                  15

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 187

Arg Glu Leu Val Asn Pro Ala Ser Met Lys Gln Ala Leu Ile Ala
 1               5                  10                  15

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: Synthetic -continued

```
<400> SEQUENCE: 188

Val Asn Pro Ala Ser Met Lys Gln Ala Leu Ile Ala Ser Ala Arg
 1               5                  10                  15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 189

Ala Ser Met Lys Gln Ala Leu Ile Ala Ser Ala Arg Arg Leu Pro
 1               5                  10                  15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 190

Lys Gln Ala Leu Ile Ala Ser Ala Arg Arg Leu Pro Gly Val Asn
 1               5                  10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 191

Leu Ile Ala Ser Ala Arg Arg Leu Pro Gly Val Asn Met Phe Glu
 1               5                  10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 192

Ser Ala Arg Arg Leu Pro Gly Val Asn Met Phe Glu Gln Gly His
 1               5                  10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 193

Arg Leu Pro Gly Val Asn Met Phe Glu Gln Gly His Gly Lys Leu
 1               5                  10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 194
```

```
Gly Val Asn Met Phe Glu Gln Gly His Gly Lys Leu Asp Leu Leu
  1               5                  10                  15
```

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 195

```
Met Phe Glu Gln Gly His Gly Lys Leu Asp Leu Leu Arg Ala Tyr
  1               5                  10                  15
```

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 196

```
Gln Gly His Gly Lys Leu Asp Leu Leu Arg Ala Tyr Gln Ile Leu
  1               5                  10                  15
```

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 197

```
Gly Lys Leu Asp Leu Leu Arg Ala Tyr Gln Ile Leu Asn Ser Tyr
  1               5                  10                  15
```

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 198

```
Asp Leu Leu Arg Ala Tyr Gln Ile Leu Asn Ser Tyr Lys Pro Gln
  1               5                  10                  15
```

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 199

```
Arg Ala Tyr Gln Ile Leu Asn Ser Tyr Lys Pro Gln Ala Ser Leu
  1               5                  10                  15
```

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 200

```
Gln Ile Leu Asn Ser Tyr Lys Pro Gln Ala Ser Leu Ser Pro Ser
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 201

Asn Ser Tyr Lys Pro Gln Ala Ser Leu Ser Pro Ser Tyr Ile Asp
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 202

Lys Pro Gln Ala Ser Leu Ser Pro Ser Tyr Ile Asp Leu Thr Glu
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 203

Ala Ser Leu Ser Pro Ser Tyr Ile Asp Leu Thr Glu Cys Pro Tyr
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 204

Ser Pro Ser Tyr Ile Asp Leu Thr Glu Cys Pro Tyr Met Trp Pro
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 205

Tyr Ile Asp Leu Thr Glu Cys Pro Tyr Met Trp Pro Tyr Cys Ser
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 206

Leu Thr Glu Cys Pro Tyr Met Trp Pro Tyr Cys Ser Gln Pro Ile
```

-continued

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 207

```
Cys Pro Tyr Met Trp Pro Tyr Cys Ser Gln Pro Ile Tyr Tyr Gly
  1               5                  10                  15
```

<210> SEQ ID NO 208
<211> LENGTH: 1052
<212> TYPE: PRT
<213> ORGANISM: Homo sapiens

<400> SEQUENCE: 208

```
Met Lys Leu Val Asn Ile Trp Leu Leu Leu Val Val Leu Leu Cys
  1               5                  10                  15

Gly Lys Lys His Leu Gly Asp Arg Leu Glu Lys Lys Ser Phe Glu Lys
                 20                  25                  30

Ala Pro Cys Pro Gly Cys Ser His Leu Thr Leu Lys Val Glu Phe Ser
         35                  40                  45

Ser Thr Val Glu Tyr Glu Tyr Ile Val Ala Phe Asn Gly Tyr Phe
     50                  55                  60

Thr Ala Lys Ala Arg Asn Ser Phe Ile Ser Ser Ala Leu Lys Ser Ser
 65                  70                  75                  80

Glu Val Asp Asn Trp Arg Ile Ile Pro Arg Asn Asn Pro Ser Ser Asp
                 85                  90                  95

Tyr Pro Ser Asp Phe Glu Val Ile Gln Ile Lys Glu Lys Gln Lys Ala
                100                 105                 110

Gly Leu Leu Thr Leu Glu Asp His Pro Asn Ile Lys Arg Val Thr Pro
                115                 120                 125

Gln Arg Lys Val Phe Arg Ser Leu Lys Tyr Ala Glu Ser Asp Pro Thr
130                 135                 140

Val Pro Cys Asn Glu Thr Arg Trp Ser Gln Lys Trp Gln Ser Ser Arg
145                 150                 155                 160

Pro Leu Arg Arg Ala Ser Leu Ser Leu Gly Ser Gly Phe Trp His Ala
                165                 170                 175

Thr Gly Arg His Ser Ser Arg Arg Leu Leu Arg Ala Ile Pro Arg Gln
                180                 185                 190

Val Ala Gln Thr Leu Gln Ala Asp Val Leu Trp Gln Met Gly Tyr Thr
                195                 200                 205

Gly Ala Asn Val Arg Val Ala Val Phe Asp Thr Gly Leu Ser Glu Lys
     210                 215                 220

His Pro His Phe Lys Asn Val Lys Glu Arg Thr Asn Trp Thr Asn Glu
225                 230                 235                 240

Arg Thr Leu Asp Asp Gly Leu Gly His Gly Thr Phe Val Ala Gly Val
                245                 250                 255

Ile Ala Ser Met Arg Glu Cys Gln Gly Phe Ala Pro Asp Ala Glu Leu
                260                 265                 270

His Ile Phe Arg Val Phe Thr Asn Asn Gln Val Ser Tyr Thr Ser Trp
                275                 280                 285

Phe Leu Asp Ala Phe Asn Tyr Ala Ile Leu Lys Lys Ile Asp Val Leu
     290                 295                 300
```

-continued

```
Asn Leu Ser Ile Gly Gly Pro Asp Phe Met Asp His Pro Phe Val Asp
305                 310                 315                 320
Lys Val Trp Glu Leu Thr Ala Asn Asn Val Ile Met Val Ser Ala Ile
            325                 330                 335
Gly Asn Asp Gly Pro Leu Tyr Gly Thr Leu Asn Asn Pro Ala Asp Gln
            340                 345                 350
Met Asp Val Ile Gly Val Gly Gly Ile Asp Phe Glu Asp Asn Ile Ala
            355                 360                 365
Arg Phe Ser Ser Arg Gly Met Thr Thr Trp Glu Leu Pro Gly Gly Tyr
370                 375                 380
Gly Arg Met Lys Pro Asp Ile Val Thr Tyr Gly Ala Gly Val Arg Gly
385                 390                 395                 400
Ser Gly Val Lys Gly Cys Arg Ala Leu Ser Gly Thr Ser Val Ala
            405                 410                 415
Ser Pro Val Val Ala Gly Ala Val Thr Leu Leu Val Ser Thr Val Gln
            420                 425                 430
Lys Arg Glu Leu Val Asn Pro Ala Ser Met Lys Gln Ala Leu Ile Ala
            435                 440                 445
Ser Ala Arg Arg Leu Pro Gly Val Asn Met Phe Glu Gln Gly His Gly
    450                 455                 460
Lys Leu Asp Leu Leu Arg Ala Tyr Gln Ile Leu Asn Ser Tyr Lys Pro
465                 470                 475                 480
Gln Ala Ser Leu Ser Pro Ser Tyr Ile Asp Leu Thr Glu Cys Pro Tyr
                485                 490                 495
Met Trp Pro Tyr Cys Ser Gln Pro Ile Tyr Tyr Gly Gly Met Pro Thr
            500                 505                 510
Val Val Asn Val Thr Ile Leu Asn Gly Met Gly Val Thr Gly Arg Ile
            515                 520                 525
Val Asp Lys Pro Asp Trp Gln Pro Tyr Leu Pro Gln Asn Gly Asp Asn
530                 535                 540
Ile Glu Val Ala Phe Ser Tyr Ser Ser Val Leu Trp Pro Trp Ser Gly
545                 550                 555                 560
Tyr Leu Ala Ile Ser Ile Ser Val Thr Lys Lys Ala Ala Ser Trp Glu
            565                 570                 575
Gly Ile Ala Gln Gly His Val Met Ile Thr Val Ala Ser Pro Ala Glu
                580                 585                 590
Thr Glu Ser Lys Asn Gly Ala Glu Gln Thr Ser Thr Val Lys Leu Pro
            595                 600                 605
Ile Lys Val Lys Ile Ile Pro Thr Pro Arg Ser Lys Arg Val Leu
610                 615                 620
Trp Asp Gln Tyr His Asn Leu Arg Tyr Pro Pro Gly Tyr Phe Pro Arg
625                 630                 635                 640
Asp Asn Leu Arg Met Lys Asn Asp Pro Leu Asp Trp Asn Gly Asp His
                645                 650                 655
Ile His Thr Asn Phe Arg Asp Met Tyr Gln His Leu Arg Ser Met Gly
                660                 665                 670
Tyr Phe Val Glu Val Leu Gly Ala Pro Phe Thr Cys Phe Asp Ala Ser
            675                 680                 685
Gln Tyr Gly Thr Leu Leu Met Val Asp Ser Glu Glu Tyr Phe Pro
            690                 695                 700
Glu Glu Ile Ala Lys Leu Arg Arg Asp Val Asp Asn Gly Leu Ser Leu
705                 710                 715                 720
```

-continued

```
Val Ile Phe Ser Asp Trp Tyr Asn Thr Ser Met Arg Lys Val Lys
            725                 730                 735

Phe Tyr Asp Glu Asn Thr Arg Gln Trp Trp Met Pro Asp Thr Gly Gly
            740                 745                 750

Ala Asn Ile Pro Ala Leu Asn Glu Leu Leu Ser Val Trp Asn Met Gly
            755                 760                 765

Phe Ser Asp Gly Leu Tyr Glu Gly Glu Phe Thr Leu Ala Asn His Asp
            770                 775                 780

Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Glu Asn Val Pro Ile Leu Gly Leu Tyr Gln
            820                 825                 830

Ile Pro Ala Glu Gly Gly Arg Ile Val Leu Tyr Gly Asp Ser Asn
            835                 840                 845

Cys Leu Asp Asp Ser His Arg Gln Lys Asp Cys Phe Trp Leu Leu Asp
            850                 855                 860

Ala Leu Leu Gln Tyr Thr Ser Tyr Gly Val Thr Pro Pro Ser Leu Ser
865                 870                 875                 880

His Ser Gly Asn Arg Gln Arg Pro Ser Gly Ala Gly Ser Val Thr
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
            915                 920                 925

Arg Leu Ser Trp Ala Lys Pro Gln Pro Leu Asn Glu Thr Ala Pro Ser
            930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln Thr Ile Pro Val Phe Ala Phe Leu
            995                 1000                1005

Gly Ala Met Val Val Leu Ala Phe Phe Val Val Gln Ile Asn Lys Ala
    1010                1015                1020

Lys Ser Arg Pro Lys Arg Arg Lys Pro Arg Val Lys Arg Pro Gln Leu
1025                1030                1035                1040

Met Gln Gln Val His Pro Pro Lys Thr Pro Ser Val
                1045                1050

<210> SEQ ID NO 209
<211> LENGTH: 280
<212> TYPE: PRT
<213> ORGANISM: Homo sapiens

<400> SEQUENCE: 209

Arg Ala Ile Pro Arg Gln Val Ala Gln Thr Leu Gln Ala Asp Val Leu
  1               5                  10                  15

Trp Gln Met Gly Tyr Thr Gly Ala Asn Val Arg Val Ala Val Phe Asp
                 20                  25                  30

Thr Gly Leu Ser Glu Lys His Pro His Phe Lys Asn Val Lys Glu Arg
             35                  40                  45
```

```
Thr Asn Trp Thr Asn Glu Arg Thr Leu Asp Asp Gly Leu Gly His Gly
 50                  55                  60

Thr Phe Val Ala Gly Val Ile Ala Ser Met Arg Glu Cys Gln Gly Phe
 65                  70                  75                  80

Ala Pro Asp Ala Glu Leu His Ile Phe Arg Val Phe Thr Asn Asn Gln
                 85                  90                  95

Val Ser Tyr Thr Ser Trp Phe Leu Asp Ala Phe Asn Tyr Ala Ile Leu
                100                 105                 110

Lys Lys Ile Asp Val Leu Asn Leu Ser Ile Gly Gly Pro Asp Phe Met
                115                 120                 125

Asp His Pro Phe Val Asp Lys Val Trp Glu Leu Thr Ala Asn Asn Val
                130                 135                 140

Ile Met Val Ser Ala Ile Gly Asn Asp Gly Pro Leu Tyr Gly Thr Leu
145                 150                 155                 160

Asn Asn Pro Ala Asp Gln Met Asp Val Ile Gly Val Gly Gly Ile Asp
                165                 170                 175

Phe Glu Asp Asn Ile Ala Arg Phe Ser Ser Arg Gly Met Thr Thr Trp
                180                 185                 190

Glu Leu Pro Gly Gly Tyr Gly Arg Met Lys Pro Asp Ile Val Thr Tyr
                195                 200                 205

Gly Ala Gly Val Arg Gly Ser Gly Val Lys Gly Gly Cys Arg Ala Leu
                210                 215                 220

Ser Gly Thr Ser Val Ala Ser Pro Val Val Ala Gly Ala Val Thr Leu
225                 230                 235                 240

Leu Val Ser Thr Val Gln Lys Arg Glu Leu Val Asn Pro Ala Ser Met
                245                 250                 255

Lys Gln Ala Leu Ile Ala Ser Ala Arg Arg Leu Pro Gly Val Asn Met
                260                 265                 270

Phe Glu Gln Gly His Gly Lys Leu
                275                 280

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 210

Ile Lys Asp Phe His Val Tyr Phe Arg Glu Ser Arg Asp Ala Gly
  1               5                  10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 211

Asp Ala Glu Leu His Ile Phe Arg Val Phe Thr Asn Asn Gln Val
  1               5                  10                  15
```

MUTANT PROTEINS HAVING LOWER ALLERGENIC RESPONSE IN HUMANS AND METHODS FOR CONSTRUCTING, IDENTIFYING AND PRODUCING SUCH PROTEINS

BACKGROUND OF THE INVENTION

A. Field of the Invention

The present invention relates to proteins which produce lower allergenic response in humans exposed to such proteins, and an assay predictive of such response. More specifically, the present invention relates to a novel improved protein mutant which produces very low allergenic response in humans sensitized to that protein through exposure compared to the precursor of such protein mutant.

B. State of the Art

Proteins used in industrial, pharmaceutical and commercial applications are of increasing prevalence. As a result, the increased exposure due to this prevalence has been responsible for some safety hazards caused by the sensitization of certain persons to those peptides, whereupon subsequent exposure causes extreme allergic reactions which can be injurious and even fatal. For example, proteases are known to cause dangerous hypersensitivity in some individuals. As a result, despite the usefulness of proteases in industry, e.g., in laundry detergents, cosmetics, textile treatment etc. . . . , and the extensive research performed in the field to provide improved proteases which have, for example, more effective stain removal under detergency conditions, the use of proteases in industry has been problematic due to their ability to produce a hypersensitive allergenic response in some humans.

Much work has been done to alleviate these problems. Among the strategies explored to reduce immunogenic potential of protease use have been improved production processes which reduce potential contact by controlling and minimizing workplace concentrations of dust particles or aerosol carrying airborne protease, improved granulation processes which reduce the amount of dust or aerosol actually produced from the protease product, and improved recovery processes to reduce the level of potentially allergenic contaminants in the final product. However, efforts to reduce the allergenicity of protease, per se, have been relatively unsuccessful. Alternatively, efforts have been made to mask epitopes in protease which are recognized by immunoglobulin E (IgE) in hypersensitive individuals (PCT Publication No. WO 92/10755) or to enlarge or change the nature of the antigenic determinants by attaching polymers or peptides/proteins to the problematic protease.

When an adaptive immune response occurs in an exaggerated or inappropriate form, the individual experiencing the reaction is said to be hypersensitive. Hypersensitivity reactions are the result of normally beneficial immune responses acting inappropriately and sometimes cause inflammatory reactions and tissue damage. They can be provoked by many antigens; and the cause of a hypersensitivity reaction will vary from one individual to the next. Hypersensitivity does not normally manifest itself upon first contact with the antigen, but usually appears upon subsequent contact. One form of hypersensitivity occurs when an IgE response is directed against innocuous environmental antigens, such as pollen, dust-mites or animal dander. The resulting release of pharmacological mediators by IgE-sensitized mast cells produces an acute inflammatory reaction with symptoms such as asthma or rhinitis.

Nonetheless, a strategy comprising modifying the IgE sites will not generally be successful in preventing the cause of the initial sensitization reaction. Accordingly, such strategies, while perhaps neutralizing or reducing the severity of the subsequent hypersensitivity reaction, will not reduce the number or persons actually sensitized. For example, when a person is known to be hypersensitive to a certain antigen, the general, and only safe, manner of dealing with such a situation is to isolate the hypersensitive person from the antigen as completely as possible. Indeed, any other course of action would be dangerous to the health of the hypersensitive individual. Thus, while reducing the danger of a specific protein for a hypersensitive individual is important, for industrial purposes it would be far more valuable to render a protein incapable of initiating the hypersensitivity reaction in the first place.

T-lymphocytes (T-cells) are key players in the induction and regulation of immune responses and in the execution of immunological effector functions. Specific immunity against infectious agents and tumors is known to be dependent on these cells and they are believed to contribute to the healing of injuries. On the other hand, failure to control these responses can lead to auto aggression. In general, antigen is presented to T-cells in the form of antigen presenting cells which, through a variety of cell surface mechanisms, capture and display antigen or partial antigen in a manner suitable for antigen recognition by the T-cell. Upon recognition of a specific epitope by the receptors on the surface of the T-cells (T-cell receptors), the T-cells begin a series of complex interactions, including proliferation, which result in the production of antibody by B-cells. While T-cells and B-cells are both activated by antigenic epitopes which exist on a given protein or peptide, the actual epitopes recognized by these mononuclear cells are generally not identical. In fact, the epitope which activates a T-cell to initiate the creation of immunologic diversity is quite often not the same epitope which is later recognized by B-cells in the course of the immunologic response. Thus, with respect to hypersensitivity, while the specific antigenic interaction between the T-cell and the antigen is a critical element in the initiation of the immune response to antigenic exposure, the specifics of that interaction, i.e., the epitope recognized, is often not relevant to subsequent development of a full blown allergic reaction.

PCT Publication No. WO 96/40791 discloses a process for producing polyalkylene oxide-polypeptide conjugates with reduced allergenicity using polyalkylene oxide as a starting material.

PCT Publication No. WO 97/30148 discloses a polypeptide conjugate with reduced allergenicity which comprises one polymeric carrier molecule having two or more polypeptide molecules coupled covalently thereto.

PCT Publication No. WO 96/17929 discloses a process for producing polypeptides with reduced allergenicity comprising the step of conjugating from 1 to 30 polymolecules to a parent polypeptide.

PCT Publication No. WO 92/10755 discloses a method of producing protein variants evoking a reduced immunogenic response in animals. In this application, the proteins of interest, a series of proteases and variants thereof, were used to immunized rats. The sera from the rats was then used to measure the reactivity of the polyclonal antibodies already produced and present in the immunized sera to the protein of interest and variants thereof. From these results, it was possible to determine whether the antibodies in the preparation were comparatively more or less reactive with the protein and its variants, thus permitting an analysis of which changes in the protein are likely to neutralize or reduce the ability of the Ig to bind. From these tests on rats, the conclusion was arrived at that changing any of subtilisin 309 residues corresponding to 127, 128, 129, 130, 131, 151, 136, 151, 152, 153, 154, 161, 162, 163, 167, 168, 169, 170, 171, 172, 173, 174, 175, 176, 186, 193, 194, 195, 196, 197, 247, 251, 261 will result in a change in the immunological potential.

PCT Publication No. WO 94/10191 discloses low allergenic proteins comprising oligomeric forms of the parent monomeric protein, wherein the oligomer has substantially retained its activity.

The prior art has provided methods of reducing the allergenicity of certain proteins and identification of epitopes which cause allergic reactions in some individuals, the assays used to identify these epitopes generally involving measurement of IgE and IgG antibody in blood sera previously exposed to the antigen. Nonetheless, once an Ig reaction has been initiated, sensitization has already occurred. Accordingly, there is a need for a method of determining epitopes which cause sensitization in the first place, as neutralization of these epitopes will result in significantly less possibility for sensitization to occur, thus reducing the possibility of initial sensitization.

SUMMARY OF THE INVENTION

It is an object of the invention to provide a protein having decreased potential to cause allergenic response in humans compared to a precursor protein.

It is a further object of the present invention to provide for a protease variant which has useful activity in common protease applications, such as detergents and or the treatment of wool to prevent felting, in bar or liquid soap applications, dish-care formulations, contact lens cleaning solutions or products, peptide hydrolysis, waste treatment, textile applications such as anti-felting, in cosmetic formulations and for skin care, or as fusion-cleavage enzymes in protein production, which protease variant can be more safely used due to its lowered allergenic potential.

According to the present invention, a method for identifying T-cell epitopes within a protein is provided. The present invention provides an assay which identifies epitopes as follows: antigen presenting cells are combined with naïve human T-cells and with a peptide of interest. In a preferred embodiment of the invention, a method is provided wherein a T-cell epitope is recognized comprising the steps of: (a) obtaining from a single blood source a solution of dendritic cells and a solution of naïve CD4+ and/or CD8+ T-cells; (b) promoting differentiation in said solution of dendritic cells; (c) combining said solution of differentiated dendritic cells and said naïve CD4+ and/or CD8+ T-cells with a peptide of interest; (d) measuring the proliferation of T-cells in said step (c).

According to another embodiment of the present invention, a protein is provided in which a T-cell epitope is modified so as to reduce or preferably neutralize (eliminate) the ability of the T-cell to identify that epitope. Thus, a protein is provided having reduced allergenicity, wherein said protein comprises a modification comprising the substitution or deletion of amino acid residues which are identified as within a T-cell epitope. According to a preferred embodiment, an epitope is determined in a protein or peptide which, when recognized by a T-cell, results in the proliferation of T-cells which is greater than the baseline. That T-cell epitope is then modified so that, when the peptide comprising the epitope is analyzed in the assay of the invention, it results in lesser proliferation than the protein comprising the unmodified epitope. More preferably, the epitope to be modified produces greater than three times the baseline T-cell proliferation in a sample. When modified, the epitope produces less than three times the baseline T-cell proliferation, preferably less than two times the baseline T-cell proliferation and most preferably less than or substantially equal to the baseline T-cell proliferation in a sample.

Preferably, the epitope is modified in one of the following ways: (a) the amino acid sequence of the epitope is substituted with an analogous sequence from a human homolog to the protein of interest, i.e., human subtilisin or another human protease derived subtilisin like molecule such as furin or the kexins (see e.g., *Methods in Enzymology*, Vol. 244., (1994) pp. 175 et seq; Roebroek et al., *EMBO J.*, Vol. 5, No. 9, pp. 2197–2202 (1986); Tomkinson et al., *Biochem.*, Vol. 30, pp. 168–174 (1991); Keifer et al., *DNA and Cell Biol.*, Vol. 10, No. 10, pp. 757–769 (1991)); (b) the amino acid sequence of the epitope is substituted with an analogous sequence from a non-human homolog to the protein of interest, which analogous sequence produces a lesser allergenic response due to T-cell recognition than that of the protein of interest; (c) the amino acid sequence of the epitope is substituted with a sequence which substantially mimics the major tertiary structure attributes of the epitope, but which produces a lesser allergenic response due to T-cell recognition than that of the protein of interest; or (d) with any sequence which produces lesser allergenic response due to T-cell recognition than that of the protein of interest.

In a specific embodiment of the invention, a protease variant is provided comprising at least one amino acid substitution at a position corresponding to residues 170, 171, 172 and/or 173 in BPN, wherein such substitutions comprise modifying residue 170 to aspartic acid, modifying residue 171 to glutamine, modifying residue 172 to methionine and/or modifying residue 173 to aspartic acid. In a most preferred embodiment, the substitution comprises modifying residues 170, 171 and 173 to aspartic acid, glutamine and aspartic acid, respectively.

In another embodiment of the present invention, a method for producing the protein of the invention having reduced allergenicity is provided. Preferably, the mutant protein is prepared by modifying a DNA encoding a precursor protein so that the modified DNA encodes the mutant protein of the invention.

In yet another embodiment of the invention, DNA sequences encoding the mutant protein, as well as expression vectors containing such DNA sequences and host cells transformed with such vectors are provided, which host cells are preferably capable of expressing such DNA to produce the mutant protein of the invention either intracellularly or extracellularly.

The mutant protein of the invention is useful in any composition or process in which the precursor protein is generally known to be useful. For example, where the protein is a protease, the reduced allergenicity protease can be used as a component in cleaning products such as laundry detergents and hard surface cleansers, as an aid in the preparation of leather, in the treatment of textiles such as wool and/or silk to reduce felting, as a component in a personal care, cosmetic or face cream product, and as a component in animal or pet feed to improve the nutritional value of the feed. Similarly, where the protein is an amylase, the reduce allergenicity amylase can be used for the liquefaction of starch, as a component in a dishwashing detergent, for desizing of textiles, in a laundry detergent or any other use for which amylase is useful.

One advantage of the present invention is that by measuring the proliferation of T-cells due to T-cell epitope recognition, it is possible to identify peptides which contain epitopes responsible for initially sensitizing an individual. That is, T-cell proliferation due to T-cell epitope recognition results in sensitization of an individual to that peptide or a protein which contains it. Neutralization of such "sensitizing" T-cell epitopes will inevitably result in a greater degree of safety for those who handle or are otherwise exposed to the antigen containing the epitope because they will not be initially sensitized, thus preventing the production of Ig antibodies typical of an allergic reaction upon subsequent exposure to the antigen.

An advantage of the present invention is the preparation of proteins, including enzymes, which may be used with significantly less danger of sensitization for the individuals exposed. Thus, for example, the proteins of the invention may be more safely used in cosmetics such as face creams, detergents such as laundry detergents, hard surface cleaning compositions and pre-wash compositions or any other use of protein, including enzymes, wherein human exposure is a necessary by-product.

BRIEF DESCRIPTION OF THE DRAWINGS

FIGS. 1A, B1, B2 and B3 illustrate the DNA (SEQ ID:NO 1) and amino acid (SEQ ID: NO 2) sequence for Bacillus amyloliquefaciens subtilisin (BPN') and a partial restriction map of this gene.

FIG. 2 illustrates the conserved amino acid residues among subtilisins from Bacillus amyloliquefaciens (SEQ ID:NO 3) and Bacillus lentus (wild-type) (SEQ ID:NO 4).

FIGS. 3A and 3B illustrate an amino acid sequence alignment of subtilisin type proteases from Bacillus amyloliquefaciens BPN', Bacillus subtilis, Bacillus licheniformis (SEQ ID:NO 5) and Bacillus lentus. The symbol * denotes the absence of specific amino acid residues as compared to subtilisin BPN'.

FIG. 4 illustrates the additive T-cell response of 16 peripheral mononuclear blood samples to peptides corresponding to the Bacillus lentus protease. Peptide E05 includes the region comprising residues corresponding to 170–173 in protease from Bacillus amyloliquefaciens.

FIG. 5 illustrates the additive T-cell response of 10 peripheral mononuclear blood samples to peptides corresponding to the human subtilisin molecule. Peptides F10, F9, F8 and F7 all contain the amino acid sequence DQMD corresponding to the region comprising residues corresponding to 170–173 in protease from Bacillus amyloliquefaciens in the sequence alignment of FIG. 3.

FIGS. 6A and 6B/6C illustrate amino acid strings corresponding to peptides derived from the sequence of Bacillus lentus protease and a human subtilisin, respectively.

FIG. 7 illustrates the amino acid sequence of human subtilisin (SEQ ID:NO 6).

FIG. 8 illustrates an amino acid sequence alignment of BPN' (Bacillus amyloliquefaciens) protease, SAVINASE (Bacillus lentus) protease and human subtilisin (S2HSBT).

FIG. 9 illustrates the T-cell response to peptides derived from Bacillus lentus protease in a sample taken from an individual known to be hypersensitive to Bacillus lentus protease. Peptide E05 represents the region corresponding to 170–173 in protease from Bacillus amyloliquefaciens.

FIG. 10 illustrates the T-cell response to various alanine substitutions in the E05 Bacillus lentus protease peptide set in a sample taken from an individual known to be hypersensitive to Bacillus lentus protease.

DETAILED DESCRIPTION OF THE INVENTION

According to the present invention, a method for identifying T-cell epitopes is provided. The present invention provides an assay which identifies epitopes as follows: differentiated dendritic cells are combined with naïve human CD4+and/or CD8+ T-cells and with a peptide of interest. More specifically, a method is provided wherein a T-cell epitope is recognized comprising the steps of: (a) obtaining from a single blood source a solution of dendritic cells and a solution of naïve CD4+ and/or CD8+ T-cells; (b) promoting differentiation in said solution of dendritic cells; (c) combining said solution of differentiated dendritic cells and said naïve CD4+ and/or CD8+ T-cells with a peptide of interest; (d) measuring the proliferation of T-cells in said step (c).

The peptide of interest to be analyzed according to the assay of the invention is derived from a protein or enzyme for which reduced allergenicity is desirable or required. In the practice of the invention, it is possible to identify with precision the location of an epitope which can cause sensitization in an individual or sampling of individuals. In a particularly effective embodiment of the invention, a series of peptide oligomers which correspond to all or part of the protein or enzyme are prepared. For example, a peptide library is produced covering the relevant portion or all of the protein. One particularly useful manner of producing the peptides is to introduce overlap into the peptide library, for example, producing a first peptide corresponds to amino acid sequence 1–10 of the subject protein, a second peptide corresponds to amino acid sequence 4–14 of the subject protein, a third peptide corresponds to amino acid sequence 7–17 of the subject protein, a fourth peptide corresponds to amino acid sequence 10–20 of the subject protein etc. . . . until representative peptides corresponding to the entire molecule are created. By analyzing each of the peptides individually in the assay provided herein, it is possible to precisely identify the location of epitopes recognized by T-cells. In the example above, the reaction of one specific peptide to a greater extent than it's neighbors will facilitate identification of the epitope anchor region to within three amino acids. After determining the location of these epitopes, it is possible to alter the amino acids within each epitope until the peptide produces a less significant T-cell response.

"Antigen presenting cell" as used herein means a cell of the immune system which present antigen on their surface which is recognizable by receptors on the surface of T-cells. Example of antigen presenting cells are dendritic cells, interdigitating cells, activated B-cells and macrophages.

"T-cell proliferation" as used herein means the number of T-cells produced during the incubation of T-cells with the antigen presenting cells, with or without antigen.

"Baseline T-cell proliferation" as used herein means T-cell proliferation which is normally seen in an individual in response to exposure to antigen presenting cells in the absence of peptide or protein antigen. For the purposes herein, the baseline T-cell proliferation level was determined on a per sample basis for each individual as the proliferation of T-cells in response to antigen presenting cells in the absence of antigen.

"T-cell epitope" means a feature of a peptide or protein which is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II major histocompatability (MHC) molecules expressed on antigen-presenting cells (see e.g., Moeller, G. ed., Antigenic Requirements for Activation of MHC-Restricted Responses, Immunological *Review,* Vol. 98, p. 187 (Copenhagen; Munksgaard) (1987).

The epitopes determined according to the assay provided herein are then modified to reduce the allergenic potential of the protein of interest. In a preferred embodiment, the epitope to be modified produces a level of T-cell proliferation of greater than three times the baseline T-cell proliferation in a sample. When modified, the epitope produces less than three times the baseline proliferation, preferably less than two times the baseline proliferation and most preferably less than or substantially equal to the baseline proliferation in a sample.

Preferably, the epitope is modified in one of the following ways: (a) the amino acid sequence of the epitope is substituted with an analogous sequence from a human homolog to the protein of interest; (b) the amino acid sequence of the epitope is substituted with an analogous sequence from a non-human homolog to the protein of interest, which analogous sequence produces a lesser allergenic response due to T-cell epitope recognition than that of the protein of interest; (c) the amino acid sequence of the epitope is substituted with a sequence which substantially mimics the major tertiary structure attributes of the epitope, but which produces a lesser allergenic response due to T-cell epitope recognition than that of the protein of interest; or (d) with any sequence which produces lesser allergenic response due to T-cell epitope recognition than that of the protein of interest.

"Sample" as used herein comprises mononuclear cells which are naïve, i.e., not sensitized, to the antigen in question.

"Homolog" as used herein means a protein or enzyme which has similar catalytic action, structure and/or use as the protein of interest. It is desirable to find a homolog that has a tertiary and/or primary structure similar to the protein of interest as replacement of the epitope in the protein of interest with an analogous segment from the homolog will reduce the disruptiveness of the change. Thus, closely homologous enzymes will provide the most desirable source of epitope substitutions. Alternatively, if possible, it is advantageous to look to human analogs for a given protein. For example, substituting a specific epitope in a bacterial subtilisin with a sequence from a human analog to subtilisin (i.e., human subtilisin) should result in less allergenicity in the bacterial protein.

An "analogous" sequence may be determined by ensuring that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids should maintain that specific structure.

While the present invention extends to all proteins for which it is desired to reduce allergenicity, for the sake of simplicity, the following will describe a particularly preferred embodiment of the invention, the modification of protease. Proteases are carbonyl hydrolases which generally act to cleave peptide bonds of proteins or peptides. As used herein, "protease" means a naturally-occurring protease or a recombinant protease. Naturally-occurring proteases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in is series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include but are not limited to the subtilisins identified in FIG. 3 herein. Generally and for purposes of the present invention, numbering of the amino acids in proteases corresponds to the numbers assigned to the mature *Bacillus amyloliquefaciens* subtilisin sequence presented in FIG. 1.

"Recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. No. 4,760,025 (RE 34,606), U.S. Pat. Nos. 5,204,015 and 5,185,258.

"Non-human subtilisins" and the DNA encoding them may be obtained from many procaryotic and eucaryotic organisms. Suitable examples of procaryotic organisms include gram negative organisms such as *E. coli* or *Pseudomonas* and gram positive bacteria such as *Micrococcus or Bacillus.* Examples of eucaryotic organisms from which subtilisin and their genes may be obtained include yeast such as *Saccharomyces cerevisiae,* fungi such as *Aspergillus* sp.

"Human subtilisin" means proteins of human origin which have subtilisin type catalytic activity, e.g., the kexin family of human derived proteases. An example of such a protein is represented by the sequence in FIG. 7. Additionally, derivatives or homologs of human subtilisin, including those from non-human sources such as mouse or rabbit, which retain the essential ability to hydrolyze peptide bonds and have at least 50%, preferably at least 65% and most preferably at least 80% homology to the protein of FIG. 7 are considered human subtilisins for the purpose of the invention.

A "protease variant" has an amino acid sequence which is derived from the amino acid sequence of a "precursor protease". The precursor proteases include naturally-occurring proteases and recombinant proteases. The amino acid sequence of the protease variant is "derived" from the precursor protease amino acid sequence by the substitution, deletion or insertion of one or more amino acids of the precursor amino acid sequence. Such modification is of the "precursor DNA sequence" which encodes the amino acid sequence of the precursor protease rather than manipulation of the precursor protease enzyme per se. Suitable methods for such manipulation of the precursor DNA sequence include methods disclosed herein, as well as methods known to those skilled in the art (see, for example, EP 0 328299, WO89/06279 and the US patents and applications already referenced herein).

The amino acid position numbers used herein refer to those assigned to the mature Bacillus amyloliquefaciens subtilisin sequence presented in FIG. 1. The invention, however, is not limited to the mutation of this particular subtilisin but extends to precursor proteases containing amino acid residues at positions which are "equivalent" to the particular identified residues in Bacillus amyloliquefaciens subtilisin. In a preferred embodiment of the present invention, the precursor protease is Bacillus lentus subtilisin and the substitutions, deletions or insertions are made at the equivalent amino acid residue in B. lentus corresponding to those listed above.

A residue (amino acid) of a precursor protease is equivalent to a residue of Bacillus amyloliquefaciens subtilisin if it is either homologous (i.e., corresponding in position in either primary or tertiary structure) or analogous to a specific residue or portion of that residue in Bacillus amyloliquefaciens subtilisin (i.e., having the same or similar functional capacity to combine, react, or interact chemically).

In order to establish homology to primary structure, the amino acid sequence of a precursor protease is directly compared to the Bacillus amyloliquefaciens subtilisin primary sequence and particularly to a set of residues known to be invariant in subtilisins for which the sequence is known. For example, FIG. 2 herein shows the conserved residues as between B. amyloliquefaciens subtilisin and B. lentus subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of Bacillus amyloliquefaciens subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, the amino acid sequence of subtilisin from Bacillus amyloliquefaciens, Bacillus subtilis, Bacillus licheniformis (carlsbergensis) and Bacillus lentus can be aligned to provide the maximum amount of homology between amino acid sequences. A comparison of these sequences shows that there are a number of conserved residues contained in each sequence. The conserved residues as between BPN' and B. lentus are identified in FIG. 2.

These conserved residues, thus, may be used to define the corresponding equivalent amino acid residues of Bacillus amyloliquefaciens subtilisin in other subtilisins such as subtilisin from Bacillus lentus (PCT Publication No. WO89/06279 published Jul. 13, 1989), the preferred protease precursor enzyme herein, or the subtilisin referred to as PB92 (EP 0 328 299), which is highly homologous to the preferred Bacillus lentus subtilisin. The amino acid sequences of certain of these subtilisins are aligned in FIGS. 3A and 3B with the sequence of Bacillus amyloliquefaciens subtilisin to produce the maximum homology of conserved residues. As can be seen, there are a number of deletions in the sequence of Bacillus lentus as compared to Bacillus amyloliquefaciens subtilisin. Thus, for example, the equivalent amino acid for Val165 in Bacillus amyloliquefaciens subtilisin in the other subtilisins is isoleucine for B. lentus and B. licheniformis.

Thus, for example, the amino acid at position +170 is lysine (K) in both B. amyloliquefaciens and B. licheniformis subtilis and arginine (R) in Savinase. In one embodiment of the protease vairants of the invention, however, the amino acid equivalent to +170 in Bacillus amyloliquefaciens subtilisin is substituted with aspartic acid (D). The abbreviations and one letter codes for all amino acids in the present invention conform to the PatentIn User Manual (GenBank, Mountain View, Calif.) 1990, p.101.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of the precursor protease and Bacillus amyloliquefaciens subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protease in question to the Bacillus amyloliquefaciens subtilisin. The best model is the crystallographic model giving the lowest R factor for experimental diffraction data at the highest resolution available.

$$R\ factor = \frac{\Sigma_h|Fo(h)| - |Fc(h)|}{\Sigma_h|Fo(h)|}$$

Equivalent residues which are functionally analogous to a specific residue of Bacillus amyloliquefaciens subtilisin are defined as those amino acids of the precursor protease which may adopt a conformation such that they either after, modify or contribute to protein structure, substrate binding or catalysis in a manner defined and attributed to a specific residue of the Bacillus amyloliquefaciens subtilisin. Further, they are those residues of the precursor protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of Bacillus amyloliquefaciens subtilisin. The coordinates of the three dimensional structure of Bacillus amyloliquefaciens subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino adds is limited to substitutions which produce a variant which has an amino acid sequence that does not correspond to one found in nature. In the case of conserved residues, such replacement should not result in a naturally-occurring sequence. The protease variants of the present invention include the mature forms of protease variants, as well as the pro- and prepro- forms of such protease variants. The prepro- forms are the preferred construction since this facilitates the expression, secretion and maturation of the protease variants.

"Prosequence" refers to a sequence of amino acids bound to the N-terminal portion of the mature form of a protease which when removed results in the appearance of the "mature" form of the protease. Many proteolytic enzymes are found in nature as translational proenzyme products and, in the absence of post-translational processing, are expressed in this fashion. A preferred prosequence for producing protease variants is the putative prosequence of Bacillus amyloliquefaciens subtilisin, although other protease prosequences may be used.

A "signal sequence" or "presequence" refers to any sequence of amino acids bound to the N-terminal portion of a protease or to the N-terminal portion of a proprotease which may participate in the secretion of the mature or pro forms of the protease. This definition of signal sequence is a functional one, meant to include all those amino acid sequences encoded by the N-terminal portion of the protease gene which participate in the effectuation of the secretion of protease under native conditions. The present invention utilizes such sequences to effect the secretion of the protease variants as defined herein. One possible signal sequence comprises the first seven amino acid residues of the signal sequence from Bacillus subtilis subtilisin fused to the remainder of the signal sequence of the subtilisin from Bacillus lentus (ATCC 21536).

A "prepro" form of a protease variant consists of the mature form of the protease having a prosequence operably linked to the amino terminus of the protease and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (RE 34,606) to render them incapable of secreting enzymatically active endoprotease. A preferred host cell for expressing protease is the Bacillus strain BG2036 which is deficient in enzymatically active neutral protease and alkaline protease (subtilisin). The construction of strain BG2036 is described in detail in U.S. Pat. No. 5,264,366. Other host cells for expressing protease include Bacillus subtilis 1168 (also described in U.S. Pat. No. 4,760,025 (RE 34,606) and U.S. Pat. No. 5,264,366, the disclosure of which are incorporated herein by reference), as well as any suitable Bacillus strain such as B. licheniformis, B. lentus, etc.

Host cells are transformed or transfected with vectors constructed using recombinant DNA techniques. Such transformed host cells are capable of either replicating vectors encoding the protease variants or expressing the desired protease variant. In the case of vectors which encode the pre- or prepro-form of the protease variant, such variants, when expressed, are typically secreted from the host cell into the host cell medium.

"Operably linked", when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protease may be obtained in accord with the general methods known to those skilled in the art. The methods generally comprise synthesizing labeled probes having putative sequences encoding regions of the protease of interest, preparing genomic libraries from organisms expressing the protease, and screening the libraries for the gene of interest by hybridization to the probes. Positively hybridizing clones are then mapped and sequenced.

The cloned protease is then used to transform a host cell in order to express the protease. The protease gene is then ligated into a high copy number plasmid. This plasmid replicates in hosts in the sense that it contains the well-known elements necessary for plasmid replication: a promoter operably linked to the gene in question (which may be supplied as the gene's own homologous promoter if it is recognized, i.e., transcribed, by the host), a transcription termination and polyadenylation region (necessary for stability of the mRNA transcribed by the host from the protease gene in certain eucaryotic host cells) which is exogenous or is supplied by the endogenous terminator region of the protease gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the protease gene into host genome. This is facilitated by procaryotic and eucaryotic organisms which are particularly susceptible to homologous recombination.

In one embodiment, the gene can be a natural gene such as that from B lentus or B. amyloliquefaciens. Alternatively, a synthetic gene encoding a naturally-occurring or mutant precursor protease may be produced. In such an approach, the DNA and/or amino acid sequence of the precursor protease is determined. Multiple, overlapping synthetic single-stranded DNA fragments are thereafter synthesized, which upon hybridization and ligation produce a synthetic DNA encoding the precursor protease. An example of synthetic gene construction is set forth in Example 3 of U.S. Pat. No. 5,204,015, the disclosure of which is incorporated herein by reference.

Once the naturally-occurring or synthetic precursor protease gene has been cloned, a number of modifications are undertaken to enhance the use of the gene beyond synthesis of the naturally-occurring precursor protease. Such modifications include the production of recombinant proteases as disclosed in U.S. Pat. No. 4,760,025 (RE 34,606) and EPO Publication No. 0 251 446 and the production of protease variants described herein.

The following cassette mutagenesis method may be used to facilitate the construction of the protease variants of the present invention, although other methods may be used. First, the naturally-occurring gene encoding the protease is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protease gene so as to facilitate the replacement of the gene segment. However, any convenient restriction site which is not overly redundant in the protease gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

In one aspect of the invention, the objective is to secure a variant protease having altered allergenic potential as compared to the precursor protease, since decreasing such potential enables safer use of the enzyme. While the instant invention is useful to lower allergenic potential, the mutations specified herein may be utilized in combination with mutations known in the art to result altered thermal stability and/or altered substrate specificity, modified activity or altered alkaline stability as compared to the precursor.

Accordingly, the present invention is directed to altering the capability of the T-cell epitope which includes residues positions 170–173 in Bacillus lentus to induce T-cell proliferation. One particularly preferred embodiment of the invention comprises making modification to either one or all of R170D, Y171Q and/or N173D. Similarly, as discussed in detail above, it is believed that the modification of the corresponding residues in any protease will result in a the neutralization of a key T-cell epitope in that protease. Thus, in combination with the presently disclosed mutations in the region corresponding to amino acid residues 170–173, substitutions at positions corresponding to N76D/S103A/V104I/G159D optionally in combination with one or more substitutions selected from the group consisting of positions corresponding to V68A, T213R, A232V, Q236H, Q245R, and T260A of Bacillus amyloliquefaciens subtilisin may be used, in addition to decreasing the allergenic potential of the variant protease of the invention, to modulate overall stability and/or proteolytic activity of the enzyme. Similarly, the substitutions provided herein may be combined with mutation at the Asparagine (N) in Bacillus lentus subtilisin at equivalent position +76 to Aspartate (D) in combination with the mutations S103A/V104I/G159D and optionally in combination with one or more substitutions selected from the group consisting of positions corresponding to V68A, T213R, A232V, Q236H, Q245R, and T260A of Bacillus amyloliquefaciens subtilisin, to produce enhanced stability and/or enhanced activity of the resulting mutant enzyme.

The most preferred embodiments of the invention include the following specific combinations of substituted residues corresponding to positions:

N76D/S103A/V104I/G159D/K170D/Y171Q/S173D; V68A/N76D/S103A/V104I/G159D/K170D/Y171Q/S173D/Q236H; V68A/N76D/S103A/V104I/G159D/K170D/Y171Q/S173D/Q236H/Q245R; V68A/N76D/S103A/V104I/G159D/K170D/Y171Q/S173D/A232V/Q236H/Q245R; and V68A/N76D///S103A/V104I/G159D/K170D/Y171Q/S173D/T213R/A232V/Q236H/Q245R/T260A of Bacillus amyloliquefaciens subtilisin. These substitutions are preferably made in Bacillus lentus (recombinant or native-type) subtilisin, although the substitutions may be made in any Bacillus protease.

Based on the screening results obtained with the variant proteases, the noted mutations noted above in Bacillus amyloliquefaciens subtilisin are important to the proteolytic activity, performance and/or stability of these enzymes and the cleaning or wash performance of such variant enzymes.

Many of the protease variants of the invention are useful in formulating various detergent compositions. A number of known compounds are suitable surfactants useful in compositions comprising the protease mutants of the invention. These include nonionic, anionic, cationic, anionic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the protease variants of the present invention may be used for any purpose that native or wild-type proteases are used. Thus, these variants can be used, for example, in bar or liquid soap applications, dishcare formulations, contact lens cleaning solutions or products, peptide hydrolysis, waste treatment, textile applications, as fusion-cleavage enzymes in protein production, etc. The variants of the present invention may comprise, in addition to decreased allergenicity, enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Proteases of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of proteases of the invention to conventional cleaning compositions does not create any special use limitation. In other words, any temperature and pH suitable for the detergent is also suitable for the present compositions as long as the pH is within the above range, and the temperature is below the described protease's denaturing temperature. In addition, proteases of the invention can be used in a cleaning composition without detergents, again either alone or in combination with builders and stabilizers.

The variant proteases of the present invention can be included in animal feed such as part of animal feed additives as described in, for example, U.S. Pat Nos. 5,612,055; 5,314,692; and 5,147,642.

One aspect of the invention is a composition for the treatment of a textile that includes variant proteases of the present invention. The composition can be used to treat for example silk or wool as described in publications such as RD 216,034; EP 134,267; U.S. Pat. No. 4,533,359; and EP 344,259.

The following is presented by way of example and is not to be construed as a limitation to the scope of the claims.

The variants can be screened for proteolytic activity according to methods well known in the art. Preferred protease variants include multiple substitutions at positions corresponding to: N76D/S103A/V104I/G159D/K170D/Y171Q/S173D; V68A/N76D/S103A/V104I/G159D/K170D/Y171Q/S173D/Q236H; V68A/N76D/S103A/V104I/G159D/K170D/Y171Q/S173D/Q236H/Q245R; V68A/N76D/S103A/V104I/G159D/K170D/Y171Q/S173D/A232V/Q236H/Q245R; and V68A/N76D/S103A/V104I/G159D/K170D/Y171Q/S173D/T213R/A232V/Q236H/Q245R/T260A of *Bacillus amyloliquefaciens* subtilisin.

All publications and patents referenced herein are hereby incorporated by reference in their entirety.

EXAMPLES

Example 1

Assay for the Identification of Peptide T-Cell Epitopes Using Naïve Human T-Cells Fresh human peripheral blood cells were collected from "naïve" humans, i.e., persons not known to be exposed to or sensitized to *Bacillus lentus* protease, for determination of antigenic epitopes in protease from *Bacillus lentus* and human subtilisin. Naïve humans is intended to mean that the individual is not known to have been exposed to or developed a reaction to protease in the past. Peripheral mononuclear blood cells (stored at room temperature, no older than 24 hours) were prepared for use as follows: Approximately 30 mls of a solution of buffy coat preparation from one unit of whole blood was brought to 50 ml with Dulbecco's phosphate buffered solution (DPBS) and split into two tubes. The samples were underlaid with 12.5 ml of room temperature lymphoprep density separation media (Nycomed density 1.077 g/ml). The tubes were centrifuged for thirty minutes at 600G. The interface of the two phases was collected, pooled and washed in DPBS. The cell density of the resultant solution was measured by hemocytometer. Viability was measured by trypan blue exclusion.

From the resulting solution, a differentiated dendritic cell culture was prepared from the peripheral blood mononuclear cell sample having a density of $10^8$ cells per 75 ml culture flask in a solution as follows:

(1) 50 ml of serum free AIM V media (Gibco) was supplemented with a 1:100 dilution beta-mercaptoethanol (Gibco). The flasks were laid flat for two hours at 37° C. in 5% $CO_2$ to allow adherence of monocytes to the flask wall.

(2) Differentiation of the monocyte cells to dendritic cells was as follows: nonadherent cells were removed and the resultant adherent cells (monocytes) combined with 30 ml of AIM V, 800 units/ml of GM-CSF (Endogen) and 500 units/ml of IL-4 (Endogen); the resulting mixture was cultured for 5 days under conditions at 37° C. in 5% $CO_2$. After five days, the cytokine TNFα (Endogen) was added to 0.2 units/ml, and the cytokine IL-1α (Endogen) was added to a final concentration of 50 units/ml and the mixture incubated at 37° C. in 5% $CO_2$ for two more days.

(3) On the seventh day, Mitomycin C was added to a concentration of 50 microgram/ml was added to stop growth of the now differentiated dendritic cell culture. The solution was incubated for 60 minutes at 37° C. in 5% $CO_2$. Dendritic cells were collected by gently scraping the adherent cells off the bottom of the flask with a cell scraper. Adherent and non-adherent cells were then centrifuged at 600G for 5 minutes, washed in DPBS and counted.

(4) The prepared dendritic cells were placed into a 96 well round bottom array at $2 \times 10^4$/well in 100 microliter total volume of AIM V media.

CD4+ T cells were prepared from frozen aliquots of the peripheral blood cell samples used to prepare the dendritic cells using the human CD4+ Cellect Kit (Biotex) as per the manufactures instructions with the following modifications: the aliquots were thawed and washed such that approximately $10^8$ cells will be applied per Cellect column; the cells were resuspended in 4 ml DPBS and 1 ml of the Cell reagent from the Cellect Kit, the solution maintained at room temperature for 20 minutes. The resultant solution was centrifuged for five minutes at 600G at room temperature and the pellet resuspended in 2 ml of DPBS and applied to the Cellect columns. The effluent from the columns was collected in 2% human serum in DPBS. The resultant CD4+ cell solution was centrifuged, resuspended in AIMV media and the density counted.

The CD4+ T-cell suspension was resuspended to a count of $2 \times 10^6$/ml in AIM V media to facilitate efficient manipulation of the 96 well plate.

Peptide antigen is prepared from a 1M stock solution in DMSO by dilution in AlM V media at a 1:10 ratio. 10 microliters of the stock solution is placed in each well of the 96 well plate containing the differentiated dendritic cells. 100 microliter of the diluted CD4+ T-cell solution as prepared above is further added to each well. Useful controls include diluted DMSO blanks, and tetanus toxoid positive controls.

The final concentrations in each well, at 210 microliter total volume are as follows:

$2 \times 10^4$ CD4+
$2 \times 10^5$ dendtritic cells (R:S of 10:1)
5 mM peptide Example 2

Identification of T-Cell Epitopes in Protease from *Bacillus lentus* and Human subtilisin Peptides for use in the assay described in Example 1 were prepared based on the *Bacillus lentus* and human subtilisin amino acid sequence. Peptide antigens were designed as follows. From the full length amino acid sequence of either human subtilisin or *Bacillus lentus* protease provided in FIG. 1, 15 mers were synthetically prepared, each 15 mer overlapping with the previous and the subsequent 15 mer except for three residues.

Peptides used correspond to amino acid residue strings in *Bacillus lentus* as provided in FIG. 8, and peptides correspond to amino acid residues in human subtilisin as provided in FIG. 7. The peptides used corresponding to the proteases is provided in FIG. 6. All tests were performed at least in duplicate. All tests reported displayed robust positive control responses to the antigen tetanus toxoid. Responses were averaged within each experiment, then normalized to the baseline response. A positive event was recorded if the response was at least 3 times the baseline response.

The immunogenic response (i.e., T-cell proliferation) to the prepared peptides from human subtilisin and *Bacillus lentus* was tallied and is provided in FIGS. 4 and 5, respectively. T-cell proliferation was measured by the incorporated tritium method. The results shown in FIGS. 4 and 5 as a comparison of the immunogenic additive response in 10 individuals (FIG. 4) and 16 individuals (FIG. 5) to the various peptides. Response is indicated as the added response wherein 1.0 equals a baseline response for each sample. Thus, in FIG. 4, a reading of 10.0 or less is the baseline response and in FIG. 5 a reading of 16.0 or less the baseline response.

As indicated in FIGS. 4 and 5, the immunogenic response of the naïve blood samples from unsensitized individuals showed a marked allergenic response at the peptide fragment from *Bacillus lentus* corresponding to residues 170–173 of *Bacillus amyloliquefaciens* protease. As expected, the corresponding fragment in human subtilisin evokes merely baseline response.

FIG. 9 shows the T-cell response to peptides derived from *Bacillus lentus* protease in a sample taken from an individual known to be hypersensitive to *Bacillus lentus* protease. Peptide E05 represents the region corresponding to 170–173 in protease from *Bacillus amyloliquefaciens*. As shown in FIG. 9, the hypersensitive individual was highly responsive to the T-cell epitope represented by the peptide E05. This result confirms that, by practicing the assay according to the invention, it is possible to predict the major epitopes identified by the T-cells of a hypersensitive individual.

FIG. 10 shows the T-cell response to various alanine substitutions in the E05 peptide derived from *Bacillus lentus* protease in a sample taken from an individual known to be hypersensitive to *Bacillus lentus* protease. Alanine substitutions were use as substitutions for the purpose of determining the role of any specific residue within the epitope. The legend of FIG. 10 refers to the position of the peptide in which an alanine was substituted, i.e., in peptide E06 (sequence GSISYPARYANAMAV),G to A=2,S to A=3I to A=4S to A=5,Y to A=6,P to A=7,R to A=8, Y to A=9, N to A=10, M to A=11 and V to A=12. As indicated in FIG. 10, substitution of either of the residues R170A, Y171A and/or N1 73A in protease from Bacillus lentus results in dramatically reduced response in the hypersensitive individual's blood sample.

From these results, it is apparent that the residues 170, 171 and 173 are critical for T-cell response within this peptide. Accordingly, it is further apparent that these residues are largely responsible for the initiation of allergic reaction within the protease from *Bacillus lentus*.

We claim:

1. A method for determining a T-cell epitope of a peptide, comprising the steps of:
   (a) obtaining from a single human blood source a solution of dendritic cells and a solution of naïve CD4+ and/or CD8+ T-cells;
   (b) differentiating said dendritic cells by exposing said dendritic cells to granulocyte-macrophage colony stimulating in factor (GM-CSF,) interleukin-4 (IL-4), tumor necrosis factor alpha (TNF-α), and interleukin-1 alpha (IL-1α);
   (c) combining said solution of differentiated dendritic cells and said naïve CD4+ and/or CD8+ T-cells with the peptide, said peptide comprising said T-cell epitope; and
   (d) measuring proliferation of said T-cells in said step (c).

2. A method of reducing the allergenicity of a protein comprising the steps of:
   (a) identifying a T-cell epitope in said protein by
      (i) contacting an adherent monocyte-derived dendritic cell that has been differentiated by exposing said dendritic cell to cytokines granulocyte-macrophage colony stimulating factor (GM-CSF), interleukin-4 (IL-4), tumor necrosis factor alpha (TNF-α), and interleukin-1 alpha (IL-1α), with a peptide comprising said T-cell epitope; and
      (ii) contacting said dendritic cell and peptide with a naïve T-cell, wherein said naïve T-cell has been obtained from the same source as said adherent monocyte-derived dendritic cell, and whereby said T-cell proliferates in response to said peptide; and
   (b) modifying said protein to neutralize said T-cell epitope such that the modified protein induces less than or substantially equal the baseline proliferation of said naïve T-cells.

3. The method according to claim 1, wherein the protein is a protease.

4. The method according to claim 2, wherein said T-cell epitope is modified by a substitution selected from the group consisting of:
   (a) substituting the amino add sequence of said T-cell epitope with an analogous sequence from a human homolog to the protein of interest;
   (b) substituting the amino add sequence of said T-cell epitope with an analogous sequence from a non-human homolog to the protein of interest; or
   (c) substituting the amino acid sequence of said T-cell epitope with a sequence which substantially mimics the major tertiary structure attributes of the epitope.

5. The method according to claim 4, wherein said T-cell epitope is modified by substituting the amino acid sequence of the T-cell epitope with an analogous sequence from a human homolog to the protein of interest.

6. The method according to claim 4, wherein said T-cell epitope is modified by substituting the amino acid sequence of said T-cell epitope with an analogous sequence from a nonhuman homolog to the protein of interest.

7. The method according to claim 4, wherein said T-cell epitope is modified by substituting the amino acid sequence of the epitope with a sequence which substantially mimics the major tertiary structure attributes of said T-cell epitope.

8. A method for reducing the allergenicity of a microbial subtilisin comprising the steps of:
   (a) determining a T-cell epitope of said subtilisin comprising (i) obtaining from a from a single human blood source a solution of dendritic cells and a solution of naïve CD4+ and/or CD8+ T-cells; (ii) promoting differentiation in said solution of dendritic cells; combining said solution of differentiated dendritic cells and said naïve CD4+ and/or CD8+ T-cells with peptide fragments of said subtilisin; and (iv) measuring proliferation of said T-cells in said step (iii); and
   (b) modifying the peptide which includes the T-cell epitope to neutralize said epitope.

9. The method according to claim 8, wherein the microbial subtilisin is derived from a *Bacillus*.

10. The method according to claim 9, wherein the *Bacillus* is selected from the group consisting of *B. lentus, B. subtilisin, B. amyloliquefaciens* and *B. licheniformis*.

11. The method according to claim 8, wherein said epitope of said microbial subtilisin is modified by: (a) substituting the amino acid sequence of the epitope with an analogous sequence from a human homolog of said microbial subtilisin; (b) substituting the amino acid sequence of the epitope with an analogous sequence from a non-human homolog of said microbial subtilisin; or (c) substituting the amino acid sequence of the epitope with a sequence which substantially mimics the major tertiary structure attributes of the epitope.

12. A method for determining a T-cell epitope of a protein, comprising the steps of:
   (a) obtaining a protein and preparing peptide fragments of said protein;
   (b) obtaining from a single human blood source a solution of dendritic cells and a solution of naïve CD4+ and/or CD8+ T-cells;
   (c) promoting differentiation of said dendritic cells by exposing said dendritic cells to granulocyte-macrophage colony stimulating factor (GM-CSF), interleukin-4 (IL-4), tumor necrosis factor alpha (TNF-α), and interleukin-1 alpha (IL-1α); (d) combining said solution of differentiated dendritic cells and said naïve CD4+ and/or CD8+ T-cells with said peptide fragments, wherein said peptide fragments comprise said T-cell epitope; and
   (e) measuring proliferation of said T-cells in said step (d).

13. A method of reducing the allergenicity of a protein comprising the steps of:
   (a) identifying a T-cell epitope in said protein by
      (i) contacting an adherent monocyte-derived dendritic cell that has been differentiated by exposure to granulocyte-macrophage colony stimulating factor (GM-CSF), interleukin-4 (IL-4), tumor necrosis factor alpha (TNF-α), and interleukin-1 alpha (IL-1α), with a peptide comprising said T-cell epitope; and
      (ii) contacting said differentiated dendritic cell and peptide with a naïve T-cell, wherein said naïve T-cell has been obtained from the same source as said adherent monocyte-derived dendritic cell, and whereby said T-cell proliferates in response to said peptide; and
   (b) modifying said protein to neutralize said T-cell epitope such that the modified protein induces less than or substantially equal the baseline proliferation of said naïve T-cells.

14. The method of claim 13, wherein said protein is a protease.

* * * * *